US006629086B1

(12) United States Patent
Lafargue et al.

(10) Patent No.: US 6,629,086 B1
(45) Date of Patent: Sep. 30, 2003

(54) METHOD FOR INTERPRETING PETROLEUM CHARACTERISTICS OF GEOLOGICAL SEDIMENTS

(75) Inventors: Eric Lafargue, Paris (FR); Bertrand Braunschweig, Clamart (FR); Wady Naanaa, Hammamet (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/450,766

(22) Filed: Nov. 30, 1999

(30) Foreign Application Priority Data

Nov. 30, 1998 (FR) .............................. 98 15102

(51) Int. Cl.[7] .............................................. G06F 15/18
(52) U.S. Cl. .............................. 706/2; 706/16; 706/929
(58) Field of Search ................................ 706/2, 16, 929

(56) References Cited

U.S. PATENT DOCUMENTS 5,751,915 A * 5/1998 Werbos ..................... 706/2

OTHER PUBLICATIONS

Shin–ichi Horikawa et al; On Fuzzy Modeling Using Fuzzy Neural Networks with the Back–Propagation Algorithm; 1992; IEEE; 9201454; 801–806.*
Masoud Nikravesh et al: Dividing Oil Fields into regions with Similar Characteristic Behavior Using Neural Network and Fuzzy Logic Approaches; 1996; IEEE; 0–7803–3225–3–6/96; 164–169.*

* cited by examiner

Primary Examiner—John Follansbee
Assistant Examiner—Joseph P. Hirl
(74) Attorney, Agent, or Firm—Antonelli, Terry, Stout & Kraus, LLP

(57) ABSTRACT

The invention relates to a method for automatic interpretation of geochemical measurements obtained by pyrolysis of a rock sample in order to obtain information pertaining to the organic matter contained in the sample. In this method, rock samples having known petroleum characteristics are used to carry out a phase of training of an artificial neural network, the neural network is used to obtain parameters pertaining to the organic matter of a rock sample, interpretation of the parameters is refined at the network output by using fuzzy sets for refining interpretation of the parameters at an output of the neural network.

3 Claims, 26 Drawing Sheets

Messages

Survey name: France
Basin name: Paris
Well name: GIRONVILLE

Eliminated samples:

Number of sample in well: 93

Distribution of samples according to OM type and maturity:

| | | |
|---|---|---|
| type II | immature | 2 |
| type II | early mature | 1 |
| type III | oil zone | 55 |
| type III | gas zone | 1 |
| type III | gas zone | 34 |

Distribution of samples according to OM type type II  1
type III  92

Distribution of samples according to maturity:

immature      2
early mature  1
oil zone      55
gas zone      35

Dominant OM type:  type III

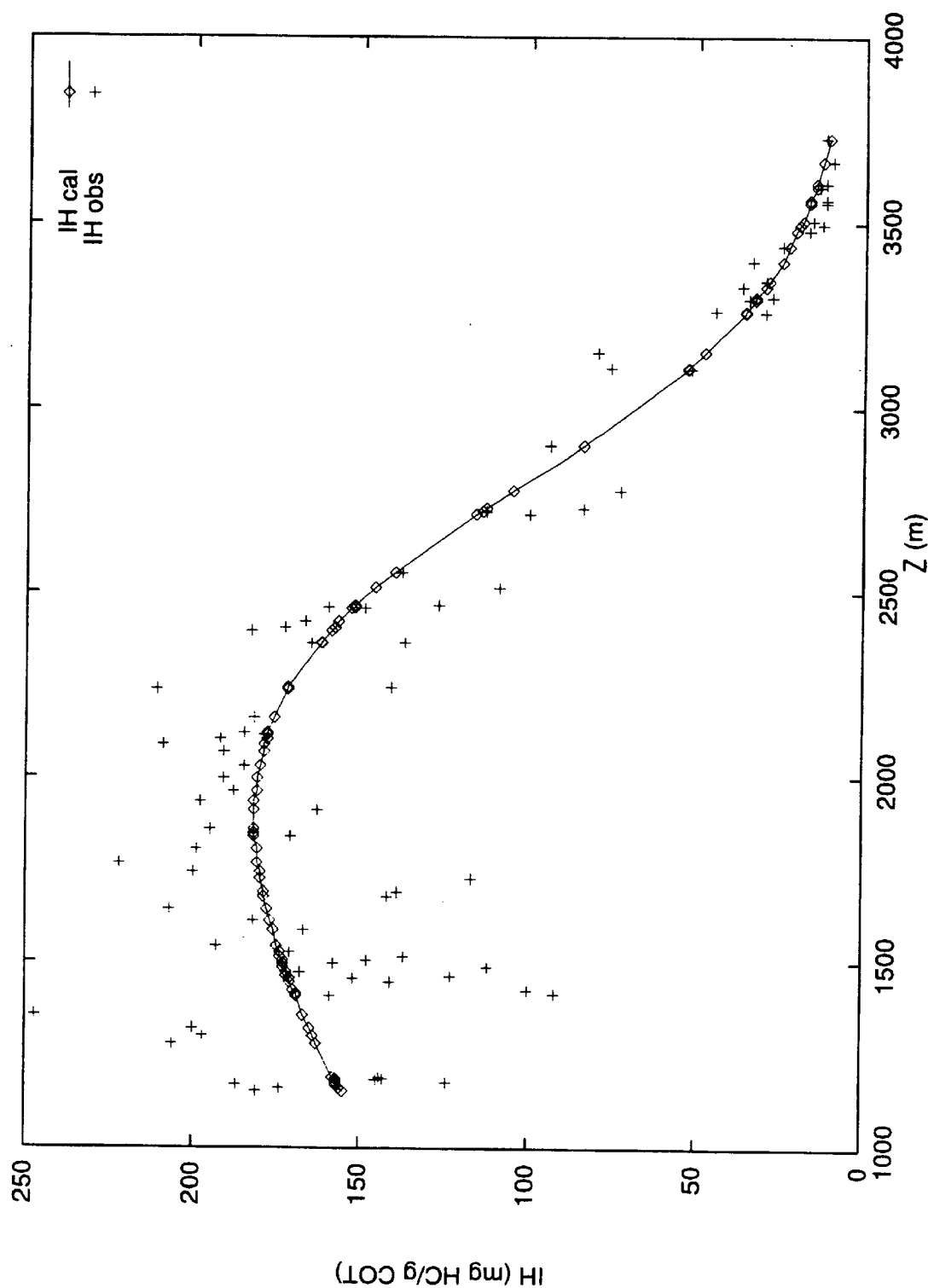

FIG. 22

| Rock-Expert analysis | |
|---|---|
| Pyrolysis data: | Diagnosis |

Pyrolysis data:
- Identifier: 2379
  - 2377
  - 2378
  - 2379
  - 2380
  - 2381
- Survey name:
- Well Name:
- Pyrolysis name: 2
- Depth: 7180.00
- Rock Eval Type: RE2
- Stage:
- Lithology:
- Nature: RB

| S0: | TMax: 429.00 |
|---|---|
| S1: 0.25 | TOC: 0.58 |
| SP1: | HI: 305.17 |
| S2: 1.77 | OI: 110.34 |
| S3: 0.64 | PI: 0.12 |
| S4: 0.41 | RCI: 0.71 |

Diagnosis:
- Comment:
- Source rock: oil source
- Petrol Potential: fair
- Accumulation: low
- Organic matter type: type II altered
- Maturity: immature Confidence level:

Organic matter type:   0        1.0
- Type I:
- Type II:
- Type III:

Maturity:
- Immature:
- Oil zone:
- Gas zone:

[✓ OK]  [✗ Cancel]  [Add]

FIG. 23

| Rock-Expert analysis | |
|---|---|
| Pyrolysis data: | Diagnosis |

Pyrolysis data:
- Identifier: 2392
  - 2390
  - 2391
  - 2392
  - 2393
  - 2394
- Survey name:
- Well Name:
- Pyrolysis name: 15
- Depth: 7900.00
- Rock Eval Type: RE2
- Stage:
- Lithology:
- Nature: RB

| S0: | TMax: 433.00 |
|---|---|
| S1: 0.20 | TOC: 0.55 |
| SP1: | HI: 320.00 |
| S2: 1.76 | OI: 67.00 |
| S3: 0.37 | PI: 0.10 |
| S4: 0.39 | RCI: 0.70 |

Diagnosis
- Comment:
- Source rock: oil source
- Petrol Potential: fair
- Accumulation: low
- Organic matter type: type II
- Maturity: early mature
- Confidence level:

Organic matter type:  0     1.0
- Type I:
- Type II: ▓▓▓▓▓▓▓▓▓▓
- Type III: ▓▓▓▓

Maturity:
- Immature: ▓▓▓▓▓▓▓▓▓▓
- Oil zone: ▓▓▓▓
- Gas zone:

[✓ OK]  [✗ Cancel]  [Add]

FIG. 24

Rock-Expert analysis

Pyrolysis data:

Identifier: 2446
- 2442
- 2443
- 2444
- 2445
- 2446

Survey name:
Well Name:
Pyrolysis name: 69
Depth: 11140.00
Rock Eval Type: RE2
Stage:
Lithology:
Nature: RB S0:          TMax: 456.00
S1: 0.35     TOC: 0.79
SP1:         HI: 279.75
S2: 2.21     OI: 24.05
S3: 0.19     PI: 0.14
S4: 0.58     RCI: 0.73

Diagnosis

Comment:
Source rock: oil source
Petrol Potential: fair
Accumulation: low
Organic matter type: type II
Maturity: oil zone Confidence level:

Organic matter type:   0          1.0
 Type I:
 Type II:
 Type III:
Maturity:
 Immature:
 Oil zone:
 Gas zone:

✓ OK     ✗ Cancel     Add

FIG. 25

Rock-Expert analysis

Pyrolysis data:

- Identifier: 2429
  - 2428
  - 2429
  - 2430
  - 2431
  - 2432
- Survey name:
- Well Name:
- Pyrolysis name: 52
- Depth: 10120.00
- Rock Eval Type: RE2
- Stage:
- Lithology:
- Nature: RB

| S0: | TMax: 444.00 |
|---|---|
| S1: 0.82 | TOC: 1.47 |
| SP1: | HI: 242.86 |
| S2: 3.57 | OI: 28.57 |
| S3: 0.42 | PI: 0.19 |
| S4: 1.11 | RCI: 0.75 |

Diagnosis

- Comment:
- Source rock: oil source
- Petrol Potential: fair
- Accumulation: low
- Organic matter type: type II
- Maturity: oil zone Confidence level:

Organic matter type: 0   1.0
- Type I:
- Type II: ▆▆▆▆▆▆
- Type III: ▪
Maturity:
- Immature:
- Oil zone: ▆▆▆▆▆▆
- Gas zone:

[✓ OK]  [✗ Cancel]  [Add]

FIG. 26

Messages

Survey name:
Basin name:
Well name:

Number of sample in well: 90

Distribution of samples according to OM type and maturity:

| | | |
|---|---|---|
| type II | immature | 1 |
| type III | immature | 1 |
| type II altered | immature | 6 |
| type II | early mature | 4 |
| type II+III | early mature | 1 |
| type II altered | early mature | 4 |
| type II | oil zone | 64 |
| type III | oil zone | 4 |
| type II+III | oil zone | 2 |
| type II altered | oil zone | 3 |

Distribution of samples according to OM type:

type II         69
type III         5
type II+III      3
type II altered 13

Distribution of samples according to maturity:

immature       8
early mature   9
oil zone      73

Dominant OM type: type II

FIG. 27

Similar sample

Pyrolysis data:

Identifier: 265
[265]

Survey name:
Well Name:
Pyrolysis name: 100306
Depth: 2556.00
Rock Eval Type: OSA
Stage: CARIXIAN
Lithology: MARL
Nature: RB S0: 0.72   TMax: 443.00
S1: 2.84   TOC: 1.95
SP1: 2.12  HI: 257.44
S2: 5.02   OI: 0.00
S3: 0.00   PI: 0.36
S4: 1.30   RCI: 0.67

Diagnosis

Comment:
Source rock: oil source
Petrol Potential: moderate
Accumulation: moderate
Organic matter type: type II
Maturity: oil zone

Confidence level:

Organic matter type:  0       1.0
 Type I:
 Type II:           [▓▓▓▓▓▓]
 Type III:
Maturity:
 Immature:          [▓▓▓▓▓▓]
 Oil zone:
 Gas zone:

[✓ OK]  [✗ Cancel]  [Add]

METHOD FOR INTERPRETING PETROLEUM CHARACTERISTICS OF GEOLOGICAL SEDIMENTS

BACKGROUND OF THE INVENTION

Field of the Invention

The present invention relates to interpretation of geochemical measurements obtained by pyrolysis of rock samples.

Description of the Prior Art

One of the objectives of organic geochemistry in oil exploration consists in characterizing the organic matter contained in source rocks. The Rock-Eval pyrolysis method (trademark registered by Institut Francais du Pétrole) has been designed to answer this need. This method allows obtaining a series of measurements which allow satisfactorily evaluation of the petroleum potential of the source rock, the amounts of free hydrocarbons contained therein, as well as the type and the maturation state of the organic matter.

Rock-Eval pyrolysis is a fast and inexpensive method allowing access to the characteristics of the organic matter. The Rock-Eval method consists in pyrolizing rock samples by heating them according to a well-determined temperature program. Pyrolysis of rock samples provides a series of parameters that are used for characterizing the organic matter contained in the pyrolysed samples.

U.S. Pat. Nos. 4,153,415, 4,352,673 and 4,519,983 illustrate the Rock-Eval method. Chapter 11.2 "Screening Techniques for Source Rock Evaluation" concerning "Rock-Eval Pyrolysis" by J. Espitalié and M. L. Bordenave in "Applied Petroleum Geochemistry", 1993, Editions Technip, France, also describes the Rock-Eval method.

SUMMARY OF THE INVENTION

The present method comprises stages using computational intelligence (IC) techniques for automatic analysis of the measurements obtained, notably through the Rock-Eval pyrolysis method. The method allows fast and reliable description of the main characteristics of the organic matter contained in source rocks.

The method is based on integration of two computational intelligence techniques, i.e. artificial neural networks and fuzzy sets. The suitability of these techniques for interpretation of the data obtained from Rock-Eval pyrolysis has allowed obtaining rapidly diagnoses that are close to and, in some cases, more accurate than diagnoses that would be made by a human expert.

The user can also have access to type samples close to those being studied.

In a variant, the analysis method allows global study of the evolution of the organic matter all along wellbores. During this analysis, the system calculates correlated relations between various geochemical data. These correlations allow the user to follow the change in the organic matter during the maturation process. The case of wellbores containing highly evolved organic matter can also be studied in order to evaluate the initial petroleum potential and the amounts of hydrocarbons that could migrate during the evolution.

The present invention thus relates to a method intended for automatic interpretation of geochemical measurements obtained by pyrolysis of a rock sample in order to obtain characterization of the organic matter contained in the sample. According to the invention, the following steps are carried out:

using rock samples having known petroleum characteristics in order to train an artificial neural network;

using the neural network to obtain parameters which pertain to the organic matter of a rock sample; and using fuzzy sets for refining interpretation of the parameters at a network output of the neural network.

The organic matter of the sample can be characterized by determining at least the type and the maturation state of the organic matter, and the petroleum potential.

An evolved series of rock samples taken during a single drilling operation can be analyzed by carrying out the following complementary stages:

from knowledge of the type of the organic matter contained in the samples, determining the correlation function f connecting the hydrogen index (HI) to the maximum pyrolysis temperature (Tmax) for the reference series of the organic matter type, determining the correlation function g connecting the hydrogen index of the evolved series to the hydrogen index of the reference series, using g and f to obtain the values of the hydrogen index as a function of depth, estimating the initial petroleum potential.

The correlation functions can be established by means of multilayer neural networks.

BRIEF DESCRIPTION OF THE DRAWINGS

FIG. 18 is a display of an example of distribution of samples;

FIGS. 19a and 19b show results obtained with the method of the invention;

FIGS. 22 to 25 show data relative to samples from well SM;

FIG. 26 shows the distribution of samples;

FIG. 27 shows data of a sample; and

DETAILED DESCRIPTION OF THE PREFERRED EMBODIMENTS

Figure 1:
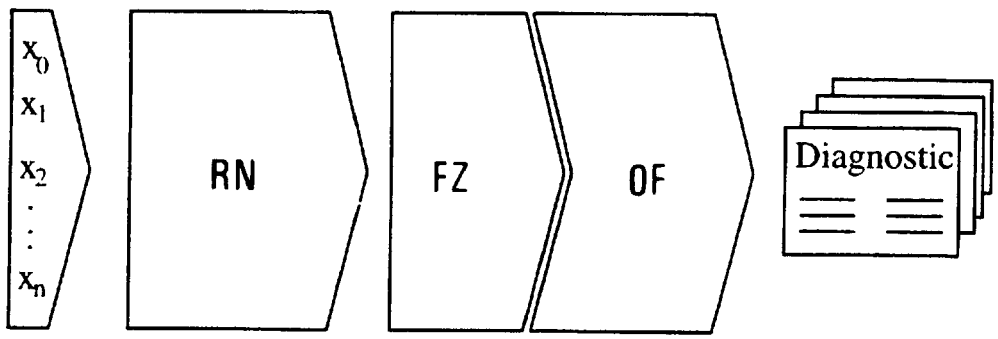
FIG. 1 is a diagram of the present invention.

Definitions allowing to better understand the methods according to the invention are given hereafter.

Free Hydrocarbons ($S_0$, $S'_1$, $S_1$):

The amounts of free hydrocarbons are given by the Rock-Eval parameter $S_1$. A distinction can be made between the hydrocarbons in the gas form given by peak $S_0$ and the hydrocarbons in the form of oil given by peak $S'_1$. Both parameters are expressed in milligrams of hydrocarbon per gram of rock.

The Petroleum Potential ($S_2$):

They are the hydrocarbon compounds resulting from cracking of kerogen during pyrolysis. They represent the total amounts of hydrocarbon compounds that can still be produced by the kerogen. These amounts are given by parameter $S_2$ that is expressed in milligrams of hydrocarbon per gram of rock.

The Oxygen Compounds ($S_3$):

The amount of $CO_2$ resulting from cracking of kerogen is given by peak $S_3$ expressed in milligrams of $CO_2$ per gram of rock.

The Organic Carbon Residue ($S_4$):

In concrete terms, it is the amount of $CO_2$ obtained by oxidation of the carbon residue fraction.

The Total Organic Carbon (TOC):

During pyrolysis, the organic carbon represents 83% of the hydrocarbon compounds that constitute $S_1$ and $S_2$. The total organic carbon is the sum of the pyrolysed organic carbon and of the organic carbon residue measured after oxidation of the sample.

The Maximum Pyrolysis Temperature ($T_{max}$):

It is the temperature at the vertex of peak $S_2$. The values of $T_{max}$ generally range between 400 and 600° C., because it is in this range that the most part of the pyrolysis occurs.

The Hydrogen Index (HI):

The hydrogen index given by the $S_2$/TOC ratio is defined from the aforementioned parameters. The hydrogen index is expressed in milligrams of hydrocarbon per gram of TOC. This index is relevant for characterization of the organic matter because it correlates quite well with the H/C atomic ratio. However, several geologic phenomena can disturb the HI values so that determination of the organic matter type from the HI alone is not very reliable.

The Oxygen Index (OI):

It is the ratio of $CO_2$ ($S_3$) to the total organic carbon (TOC). The oxygen index is therefore expressed in milligrams of $CO_2$ per gram of TOC. This index is relevant for characterization of the organic matter because it correlates quite well with the O/C atomic ratio.

The Carbon Residue Index (CRI):

It is the ratio of carbon residue ($S_4$) to the total organic carbon (TOC).

The Production Index (PI):

The production index is defined by the $S_1/(S_1+S_2)$ ratio. This index allows relative assessment of the hydrocarbon accumulations in the rock. Three criteria are taken into account to characterize source rocks: organic matter type, maturation of the organic matter and petroleum potential.

Organic matter type: there are three main types of organic matter:
  type I organic matters of lacustrine origin,
  type II organic matters of marine origin,
  type III organic matters of continental origin.

The organic carbon content is not sufficient to determine the type of organic matter contained in source rocks. The organic matter type is a relevant element in source rock characterization because it allows to estimate the hydrocarbon productivity. In fact, for the same organic carbon content, organic matters of different origins will not have the same productivity: type I organic matters can yield up to 80% by weight of hydrocarbon compounds as against 50 to 60% for types II and 15 to 30% for types III.

It can furthermore be pointed out that mixtures of organic matters are possible. There can be mixtures of type I and type II, of type I and type III, and of type II and type III. Mixtures of types I, II and III are geologically unlikely.

Maturation of the organic matter: determination of the degree of maturation of the organic matter is a relevant element in the characterization thereof. The degree of maturation of the organic matter informs about the thermal history of the source rock and, consequently, it allows knowing whether a significant amount of oil has been or might still be produced.

Petroleum potential: the quality of a source rock depends on the amount of hydrocarbons it is likely to produce. The quality of a source rock can therefore be expressed by its petroleum potential (or genetic potential).

The method allowing inferring, from Rock-Eval data, a diagnosis informing about the petroleum potential of source rocks, the type and the maturity of the organic matter contained therein and the free hydrocarbons accumulated therein is described hereafter.

The approach comprises two main components the first component uses neural techniques and the second component is based on fuzzy sets (FIG. 1: RN=neural networks; FZ=fuzzification; OF: fuzzy operators). The neural component consists of two neural networks allowing a primary analysis of the type and of the maturation of the organic matter. This first analysis is later refined by means of the fuzzy component.

Unlike the type and the maturity of the organic matter, the petroleum potential and the accumulations are relatively simpler to characterize. In fact, the petroleum potential depends on the amount of hydrocarbon compounds resulting from cracking of kerogen, and the accumulations are judged from the absolute and relative amounts of free hydrocarbons. It can be noted that it is interesting to make a distinction between normal accumulations and accumulations caused by contamination of the rock by hydrocarbons coming from somewhere else. The latter elements are analyzed by means of operations on fuzzy sets in order to qualify the automatic interpretation of Rock-Eval data.

Determination of the type and of the maturation of the organic matter is essentially based on two neural networks. The reasons that guided the selection of the neural networks are as follows:

a classification problem: characterization of the organic matter type consists in selecting a type from a certain number of predetermined types. Similarly, for maturity, one globally tries to place the state of maturity of the organic matter in a zone among several predetermined evolution zones. In both cases, it is desired to determine a category to which the organic matter belongs. It is therefore a classification problem, a type of problem for which neural networks are particularly suited;

ill-defined categories: allocating a sample to a category or another is done on the basis of parameters given by the Rock-Eval pyrolysis. The frontiers between the different categories are not known with precision, i.e. it is not known how to define the mathematical limits allowing separation of the categories from each other according to the values of the Rock-Eval parameters. Furthermore, the state of advanced maturation, the deterioration of the organic matter, the mineral matrix effects and the contamination of the organic matter complicate the classification task still more. In fact, the effect of these phenomena is that pyrolysis of a sample of a category C gives Rock-Eval parameter values that are to those of another category C' distinct from C.

TABLE 1

Rock-Eval data for two samples of different organic matter types

| | Wellbore | $S_2$ | $T_{max}$ | TOC | HI |
|---|---|---|---|---|---|
| 1 | M | 0.31 | 442 | 0.15 | 222 |
| 2 | G | 160 | 436 | 72.30 | 206 |

Consider by way of example the two samples whose Rock-Eval parameters are given in Table 1. It can be observed that these samples have rather similar $T_{max}$ and hydrogen index values. According to the $T_{max}$-HI and OI–HI diagrams (FIGS. 2 and 3) used by experts for "manual" determination of the organic matter type, both type II and type III are possible. In fact, the values of the parameters obtained for samples 1 and 2 (Table 1) are located, in the $T_{max}$-HI diagram and in the OI–HI diagram, in a zone where types II and III are possible. In actual fact however, the two samples have different origins, because sample 1 is of marine origin (type II organic matter) and sample 2 comes from a coal rock, it is therefore of continental origin (type III organic matter).

In order to distinguish between these two samples, it is sufficient to take their organic carbon content into account, which is substantially different for the two samples. Such a high TOC value (72.30%) is characteristic of coals (type III).

This example shows that, in order to obtain better discrimination between the different types of organic matter, it is advantageous to integrate, in a single interpretation process, as many Rock-Eval parameters as possible. This can be done according to the invention by means of neural networks.

Rock-Eval data are essentially numerical. Using conventional artificial intelligence tools such as production rules or decision trees implies comparisons with particular numerical values previously defined by experts. These limiting values are set, empirical and subjective, leading to sudden passage from one category of organic matter to another, whereas neural networks allow more balanced processing of the numerical data, which allows simulation of progressive passage from one category to another.

Figure 4:
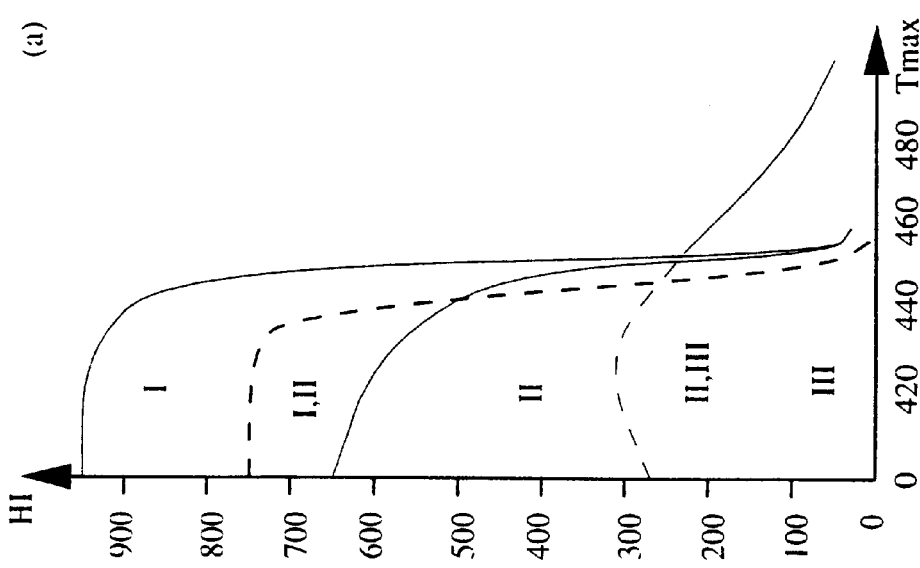
FIG. 4 shows different evolution stages of an organic material.

The diagram of FIG. 4 shows the different evolution stages of the organic matter for each organic matter type (Im=immature zone; O=oil; WG=wet gas; GS=dry gas; NT: zone of nonexistence of $T_{max}$). It can be observed that interpretation of parameter $T_{max}$, which is considered as the main maturation indicator, differs according to the type of organic matter. Using the diagram of FIG. 4 for determination of the organic matter maturity implies that the organic matter type is already known.

Furthermore, the Rock-Eval data used by experts to determine the organic matter type (notably HI, OI and $T_{max}$) are interpreted differently according to whether the organic matter is mature or not. In order to diagnose a type I for example, experts require a high HI (from 750 mg HC/g TOC) if the sample is immature, whereas the expert would be content with a HI of 500 mg HC/g TOC if the sample were already in the oil window.

This interdependence of the maturation and of the organic matter type makes interpretation of the Rock-Eval parameters by means of production systems difficult because the latter are fundamentally sequential and therefore imply knowledge of one of the elements in order to determine the other. A base consisting of wisely selected examples is used to develop and to apply the present method.

The example base contains 320 samples carefully selected from the thousands of samples available. A selection strategy is necessary for the examples selected to be representative of the whole population. The strategy used is as follows. All the available samples are scanned. For each sample, samples that are at most at a given distance d from the current sample are sought in the current example base. If there are no more than p samples (p being a given density factor) meeting this condition, the current sample is added to the example base. The distance used is defined below.

Table 3 shows the distribution of the samples of the example base among the different categories. In the base, samples with an unsure diagnosis are avoided. These samples are often those whose Rock-Eval parameters lie on the borderline between two different categories. Classification of such samples is done according to the network weight adjustments performed during the training stage.

TABLE 3

Distribution of the samples of the example base among the different organic matter classes

| | Type I | Type II | Type III |
|---|---|---|---|
| Immature | 35 | 60 | 25 |
| Oil window | — | 70 | 70 |
| Gas window | — | — | 60 |

Development of computational or artificial intelligence has allowed implementation of a multitude of computer methods and techniques allowing coding and solving problems from various fields. The method includes here two distinct tools which are the artificial neural networks and the fuzzy sets.

There are several network models that are more or less suitable according to the type of problem to be solved. The model used here is the multilayer model.

Figure 5:
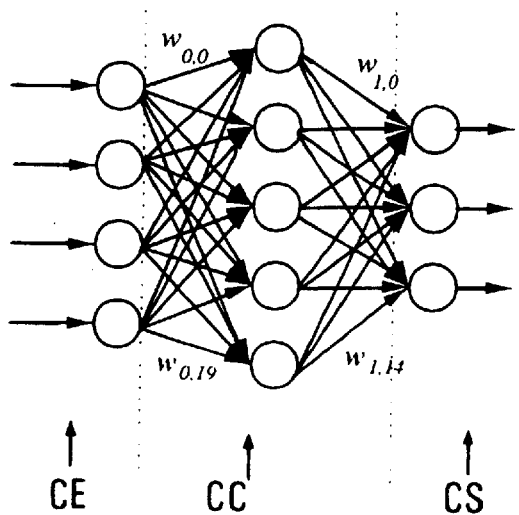
FIG. 5 shows a neural network model.

As the name indicates, a multilayer network consists of a succession of neuron layers (FIG. 5). The layer that receives the data of the problem, is referred to as input layer CE. The layer that gives the response of the network is called output layer CS. The intermediate layers, if there are any, are referred to as hidden layers CC. Each layer is connected to the layer that precedes it by inter-neuron connections. A weight is associated with each connection.

A neural network calculates outputs by propagating the activations of neurons from the input layer to the output layer. Each neuron starts by adding the weighted activations received from the layer that precedes the layer to which it belongs. The neuron applies an activation function to the weighted sum obtained in order to determine its own activation. Then, it transmits this activation to the neurons of the next layer. The most commonly used activation function is a sigmoid, more precisely the logistic function $1/(1+e^x)$ where variable x is nothing but the weighted sum of the neuron inputs. Each layer contains a predetermined number of neurons. The number of neurons of the input layer and that of the output layer are determined from the coding of the problem. The number of hidden layers and the number of neurons in each hidden layer is less easy to determine. These data are however very important because the capacity of the network to learn and to generalize depends thereon. A strategy that affords the advantage of being reliable has been used therefore. This strategy consists in starting from a minimum number of hidden layers and of neurons per hidden layer, then in adding additional layers and neurons until the network response cannot be improved any more.

The network learns how to solve the problems in question during a stage referred to as training stage, by using the base of examples already solved. Each example is defined by an input value vector and by an output value vector. The output vector contains the values that are sought by presenting the network with the associated input vector. A multilayer network therefore implements a function which associates a given input value vector with an output value vector.

The examples as a whole are divided into training examples and validation examples. This strategy, referred to as "stropped training", is intended to prevent the network from taking specific features peculiar to the training examples for relevant information. This might distort interpretation of new data which do not necessarily have the same specific features.

The training stage consists in presenting the network with the training examples one by one. The network calculates its outputs every time. Since the weights of the connections are randomly initialized, the desired output values will not be obtained straight away. Therefore, in order to make the output values obtained converge to the desired output values, the difference between these two value vectors is calculated and this difference is used to modify the weight of the connections. Modification of the weight of the connections is performed in the opposite direction to the direction of propagation of the activations during calculation of the network outputs, i.e. from the output layer to the input layer, hence the name of the training algorithm: gradient retropropagation.

The validation stage that follows each training stage consists in evaluating the network response for the validation examples, by comparing the network responses with the desired outputs for the validation examples. The alterations made to the weight of the connections during the training stage are taken into account only if the network response for the validation examples is improved.

The training and validation stages follow one another until the error obtained on the validation examples exceeds, by a predetermined threshold value, the error obtained on the training examples, in which case the algorithm stops.

The theory of fuzzy sets is a mathematical method that allows, among other things, overcoming an inadequacy of the theory of conventional sets to describe imperfectly defined classes. In the present case, the objective that is desired from the fuzzy sets is formalization of the expert's knowledge, i.e. generally empirical and subjective knowledge.

Let there be a reference set (or universe) U, a fuzzy set A is defined in U by an application $\mu_A$ of U in the real interval [0,1]. A value PA(x) such that $0 \leq \mu_A(x) \leq 1$ is associated with any element x∈U. $\mu_A$ is called belonging function of fuzzy set A.

Using fuzzy sets to describe imperfectly defined classes leads to combining these fuzzy sets in order to gain access to the usual notions of intersection, union, etc.

These combinations are obtained by means of functions of [0,1]×[0,1] in [0,1], called triangular norm and conorm (or t-norm and t-conorm).

There are several t-norms and associated t-conorms. The simplest and the most commonly used ones are those introduced by L. Zadeh (denoted by "min-max") and those introduced by Larsen (also called probabilistic t-norm).

These t-norms and their associated t-conorms are defined in Table 4.

TABLE 4

Definitions of the min-max and probabilistic t-norms and of their associated t-conorms.

| Name | t-norm | t-conorm |
| --- | --- | --- |
| Min-Max | T(x,y) = min(x,y) | ⊥(x,y) = max(x,y) |
| Probabilistic | T(x,y) = x,y | ⊥(x,y) = x+y−x,y |

The probabilistic t-norm has been preferred because the fuzzy sets to be handled are defined from results given by multilayer neural networks. Now, the outputs of multilayer neural networks express belonging probabilities. The probabilistic t-norm is therefore more suited to our problem than the "min-max" t-norm.

Let A and B be two fuzzy sets having $\mu_A$ and $\mu_B$ as their belonging functions. The probabilistic t-norm and its associated t-conorm-allow defining the belonging functions of the fuzzy sets obtained by applying the following set operators that will be used:

The complement of fuzzy set A, denoted by $\bar{A}$, is defined by the $$\mu_{\bar{A}}(x)=1-\mu_A(x).$$

belonging function

The intersection of fuzzy sets A and B, denoted by A∩B, is defined by the belonging function. The union of fuzzy sets A and B, denoted by A∪B, is defined by the belonging function $$\mu_{A \cap B}(x)=\mu_A(x).\mu_B(x).$$

$$\mu_{A \cup B}(x)=\mu_A(x)+\mu_B(x)-\mu_A(x).\mu_B(x).$$

The difference of fuzzy sets A and B, denoted by A⊖B, is defined by the $$\mu_{A \ominus B}(x)=\mu_A(x).\mu_{\bar{B}}(x)$$

belonging function

The symmetrical difference of fuzzy sets A and B, denoted by AΔB=(A⊖B)∪(B⊖A), is defined by the belonging function The networks used are multilayer networks and the training algorithm is $$\mu_{A \Delta B}(x)=\mu_{(A \ominus B) \cup (B \ominus A)}$$

that of the retropropagation of the stochastic gradient.

The type and the maturation of the organic matter are analyzed separately by two distinct neural networks called type network and maturation network. Separate networks have been selected for modularity reasons. In fact, in case wrong diagnoses are obtained for new data, independent networks allow modification of only the network concerned.

The network described hereafter allows giving a first assessment of the type of organic matter contained in a rock.

In order to select the Rock-Eval parameters that are relevant for determination of the organic matter type, the procedure followed by experts is used.

Figure 2:
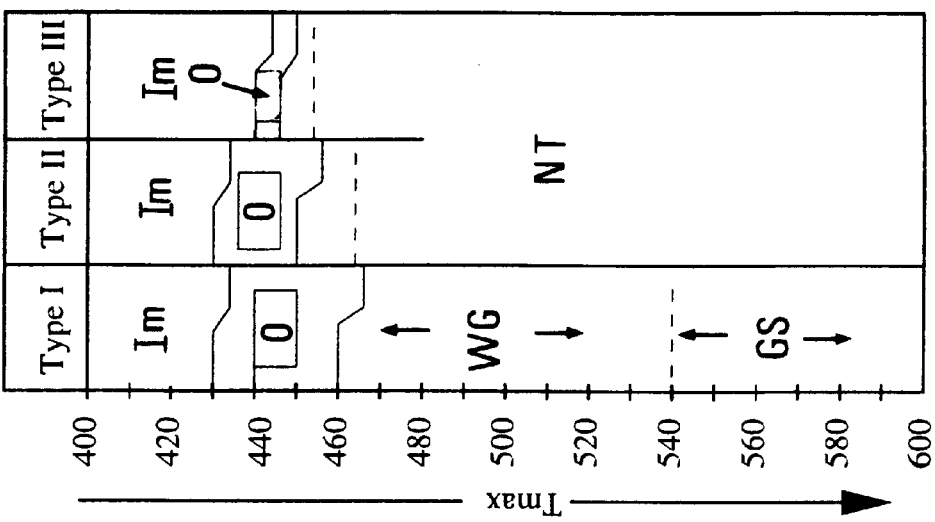
FIGS. 2 and 3 are diagrams Tmax-HI and OI–HI.
Figure 3:
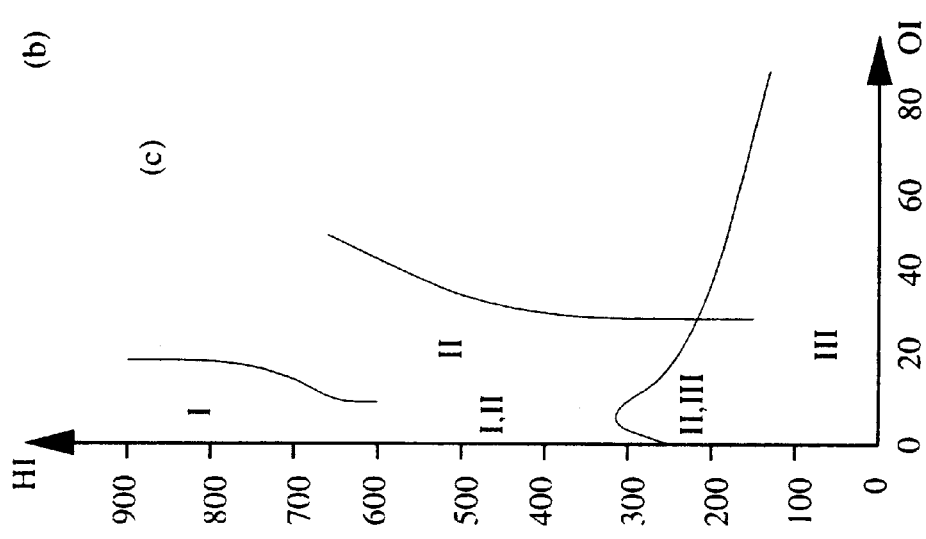

The expert essentially uses the $T_{max}$-HI and OI–HI diagrams (FIGS. 2 and 3). Given the values of $T_{max}$, HI and OI, the co-ordinates of points ($T_{max}$, HI) and (OI, HI) are formed. Each of these points is located on the corresponding diagram. The type of organic matter is the type to which the zones in which the two points lie corresponds. In most cases, the two diagrams give the same diagnosis. However, for certain borderline cases, different responses may be obtained, which is one of the drawbacks of this method.

Overlaps can be noticed on these two diagrams between the different categories. Overlaps can be more considerable in the presence of deterioration of the organic matter or of a great mineral matrix effect. In fact, these phenomena lead to a hydrogen index decrease and to an oxygen index increase. These disturbances lead to a greater overlap between type I and type II on the one hand, and between type II and type III on the other hand.

It should be pointed out that the limits between the different categories in both diagrams are empirically determined.

It can be concluded from the previous discussion that the $T_{max}$-HI and OI–HI diagrams are inadequate to reliably and unambiguously determine the organic matter type of a source rock.

The remedies of the present method which obtain better discrimination between the different types of organic matter are as follows: better use of Rock-Eval data, determination of the organic matter types based on a wider and therefore more representative range of samples, finally, qualified diagnoses to avoid sudden passage from one type of organic matter to another.

These points are achieved by taking the following measures: considering more Rock-Eval parameters as network inputs, making up an example base containing samples from several wellbores, using real-value network outputs to be able to simulate progressive passage from one category to another.

The neural network dedicated to analysis of the organic matter type comprises three layers. An input layer comprises eight inputs. Each input receives the values of one of the following eight Rock-Eval parameters: $S_2$, $S_3$, $S_4$, TOC, $T_{max}$, HI, OI and CRI. A hidden layer also comprises eight neurons. The number of neurons of this layer has been set by using the strategy of optimization of the network response described above. Finally, an output layer comprises three neurons. Each one of these neurons is associated with one of the three basic types (type I, type II and type III). The outputs take on real values in the [0,1] range.

When a sample of the example base is identified as belonging to type i, the i-th output of the network must respond by a maximum activation, whereas the other two neurons must respond by activations close to zero.

This first analysis of the organic matter types will be validated and refined by means of operations on fuzzy sets.

The main parameter for estimation of the organic matter maturation is the maximum pyrolysis temperature ($T_{max}$), an increase in the values of $T_{max}$ being observed when the evolution state of the organic matters progresses. Other indicators can also give information about the maturity state of organic matters. The hydrogen index, the oxygen index and the carbon residue index constitute appreciable additional information for maturation diagnosis. In general, a decrease in the two former indices and an increase in the latter are observed when the organic matter evolves. The relative and absolute amounts of free hydrocarbons (PI and $S_1$) can generally give information about the state of maturation since these two amounts increase in the mature phase. Including parameters TOC and $S_2$ in the input values of the maturation analysis dedicated network allows improving the behavior of the network in the training stage (where a convergence acceleration of the training algorithm is observed) and in the operating stage (where better response of the network is obtained, which is translated into more marked activation differences between the various output neurons). TOC and $S_2$ are thus used as inputs for the maturation network.

As it is the case for analysis of the organic matter type, the results given by the network dedicated to maturation analysis are refined and validated by means of operations on fuzzy sets.

The outputs of the two neural networks do not always allow unambiguous determination of the sample category. This is essentially due to the existence of ill-defined categories such as, for example, mixtures of organic matter types or intermediate states of maturation.

The simplest interpretations take place when one of the network output neurons shows a higher activation than the other neurons. In this case, it is possible to determine the category of the sample as the category associated with the neuron having the highest activation. Unfortunately, such activations are not always obtained in practice. For example, if the sample contains a mixture of organic matters, several partly activated neurons are obtained at the output of the network allowing diagnosis of the types. In this case, interpretation is less simple than in the previous case.

The purpose of integration of a fuzzy component is to continue to infer accurate and reliable diagnoses even when the neural networks provide ambiguous responses. To reach this objective, the neural component has been reinforced by a fuzzy component. The interest of this fuzzy component can be summed up as follows:

it allows interpretation of neural network responses when the networks fail to give a precise diagnosis, it allows qualification of diagnoses so as to be more in touch with reality, it allows expressing diagnoses in a language that is close to the natural language to be readable even by a user who is not familiar with Rock-Eval.

The first stage consists in fuzzifying the Rock-Eval parameters and the outputs of the two neural networks. These fuzzifications are described hereafter.

The various fuzzy sets are defined, which inevitably introduces some arbitrariness in the problem formalization. However, the fuzzy operations that will be done afterwards are based on rigorous mathematical foundations which are those of the theory of fuzzy sets.

As for the belonging functions involved in the definition of the fuzzy sets, trapezoid functions have been selected because they are easy to handle. It can be noted that the Rock-Eval parameters are not fuzzified prior to being used by the networks. However, the saturation functions are applied thereto.

Evaluation of the petroleum potential and of the hydrocarbon accumulations is performed without using neural networks. These elements will be described in the final diagnosis by linguistic values such as good, bad, high, low. The Rock-Eval parameters that require "fuzzification" are $S_1$, $S_2$, TOC, OI and PI.

Reasoning by value ranges is used because the available knowledge is incomplete. Three value ranges have been distinguished to describe these reasoning stages: low values, moderate values and high values. These value ranges are coded by fuzzy sets. Each Rock-Eval parameter is described by three fuzzy sets, each fuzzy set codes a value range.

Figure 6A:
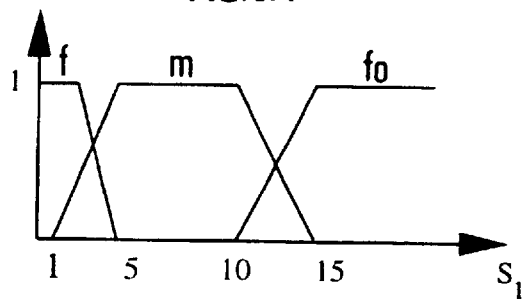
FIGS. 6, 7 and 8 describe functions of the fuzzy sets.
Figure 6B:
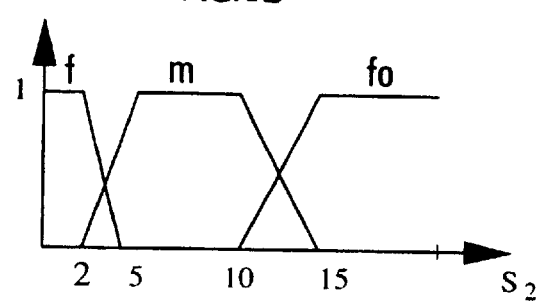
Figure 7A:
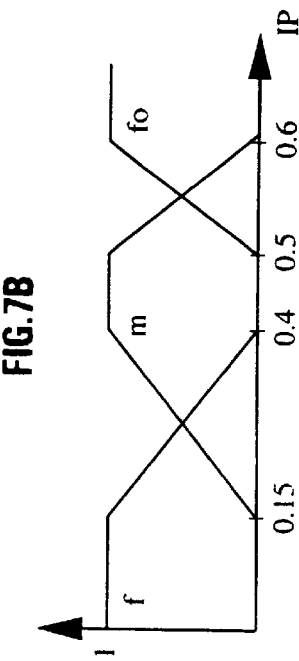
Figure 7B:
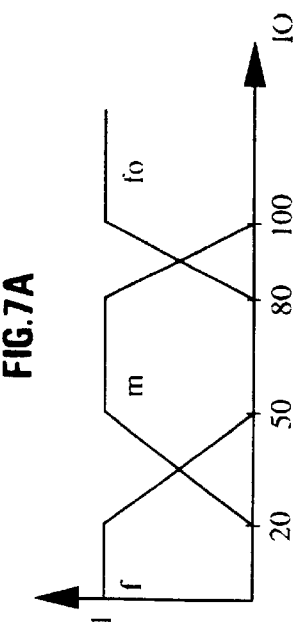
Figure 8:
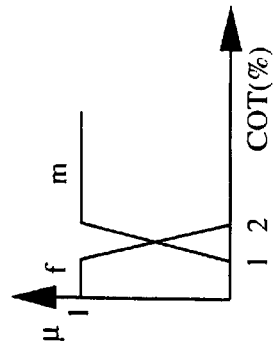

The belonging functions of the nine fuzzy sets involved in the fuzzification of parameters $S_1$, $S_2$, TOC, OI and PI are shown in FIGS. 6, 7 and 8 wherein f=low, m=moderate and of=high.

In order to obtain reliable results from interpretation of the neural component, the outputs of the two networks are first fuzzified.

Theoretically, activation of an output neuron corresponding to a category C expresses the probability of the example presented to the network belonging to category C. When the activations of all the output neurons are below a certain threshold, which means that it is unlikely that the sample belongs to one of the categories listed, it is advisable to refrain from deducing a diagnosis that might be wrong.

Figure 9:
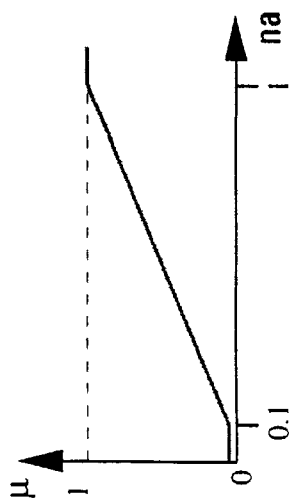
FIG. 9 describes a function between a degree and an activation level.

The objective of network output fuzzification is to consider too low activations to be zero, and to consider activations close to the maximum activation to be maximum. This fuzzification is based on six fuzzy sets: probable type I, probable type II and probable type III for the network dedicated to analysis of the organic matter types, and Immature, Oil window and Gas window for the network dedicated to maturity analysis. The belonging function used is the same for the six sets (FIG. 9). This function assigns a zero belonging degree $\mu$ to the activations below 0.1 since this activation level (na) is quite often obtained for examples where the network is supposed to respond by a zero activation. A belonging degree $\mu$ equal to 1 is assigned to activations that exceed 0.9. Finally, belonging degrees proportional to activations ranging between 0.1 and 0.9 are assigned.

The second function of the fuzzy component consists in combining the various fuzzy sets obtained during the fuzzification stage to refine the terms of the final diagnosis and to make them more reliable.

By means of fuzzy operators, characterization of the type and of the maturation of the organic matter is refined still further by distinguishing intermediate categories such as mixtures of organic matters, deteriorated organic matters and those which have undergone a great mineral matrix effect, or intermediate maturity zones.

Unlike the type and the maturation of the organic matter, the petroleum potential and the hydrocarbon accumulations are characterized only by means of fuzzy operators. These two characteristics are quantitative; it is possible, when the values of the Rock-Eval parameters are limiting values, to use vague semantic concepts such as rather, more or less . . . It can also be noted that, in the final diagnosis, the system signals coal source rocks to the user.

The basic operators selected for combining the various fuzzysets are the probabilistic t-norm and its associated t-conorm. The probabilistic t-norm has been preferred to the t-norm defined by L. Zadeh (using min and max functions) because the probabilistic t-norm combines the two degrees of belonging to the initial fuzzy sets even if one of these degrees is lower than the other, whereas the "min-max" t-norm only stores the lower belonging degree for the t-norm and the higher degree for the t-conorm.

There are three basic organic matter types: type I, type II and type III, and that the neural network dedicated to determination of the organic matter type comprises an output for each basic type. Fuzzification of the three network outputs has given the probable type I, probable type II and probable type III fuzzy sets.

The logic selected to define the basic types is based on the following reasoning diagnosis of a type i is all the more probable since the other two are unlikely.

Besides these basic types, there are two intermediate types that are useful to distinguish because they are frequently found in nature. These types are halfway between types I and types II on the one hand, and between types II and types III on the other hand. They are referred to as type I,II and type II,III respectively. Their coding is performed in such a way that the types network responds by 50% activations of the two output neurons concerned and by a zero activation of the third neuron. For example, for type I,II, neurons 1 and 2 are activated at 50% and neuron 3 shows a zero activation.

Each intermediate type comprises three sub-classes according to the geologic reason why the organic matter in question cannot be classified in one of the basic types. These sub-classes are the deteriorated organic matters, the organic matters that have undergone a great mineral matrix effect and the mixtures of organic matters.

If the organic matter has suffered deterioration, the deterioration should be detected. In fact, deterioration leads to an appreciable variation of the Rock-Eval data, notably for the oxygen index and the hydrogen index. In general, deterioration of the organic matter leads to a decrease in the hydrogen index and to an increase in the oxygen index. Now, these two indices are relevant for determination of the organic matter type. Type III coal rocks often exhibit hydrogen index values that are high enough to be mistaken for hydrogen index values of deteriorated type II organic matter. In general, types II and III on the one hand and types I and II on the other hand can be mistaken one for the other because of deterioration.

In the presence of deterioration, the network dedicated to determination of the organic matter type responds by a partial activation of its outputs. In order to make sure that this partial activation is not due to a mixture of organic matters, the network response is combined with an evaluation of the oxygen index, which is the most revealing indicator of deterioration.

Two secondary categories are thus introduced for the organic matter type: deteriorated type I and deteriorated type II.

Retention of organic matter by the mineral matrix has a disruptive effect on the Rock-Eval parameters. In fact, in the case of a great mineral matrix effect, the hydrogen index values are underestimated whereas the values of $T_{max}$ increase. This, on the one hand, makes determination of the type and of the maturation of the organic matter more problematic and, on the other hand, makes evolution of the organic matter atypical, which is the reason why it is useful to distinguish matters with a great mineral matrix effect from the rest of the organic matters.

The retention effect due to the mineral matrix is all the greater as the organic carbon content of the source rock is low. Distinction between organic matter that has undergone a great mineral matrix effect and the other sub-classes of intermediate organic matter (i.e. deteriorated organic matter and mixture of organic matters) is made on the basis of the organic carbon content of the rock. More precisely, it is agreed to identify a great mineral matrix effect in the presence of an intermediate type and when the organic carbon content has a very low probability.

Besides these basic types, there may be mixtures of organic matters, notably mixtures of types I and II on the one hand, and mixtures of types II and III on the other hand. Mixtures of organic matters are difficult to diagnose, even for an expert. As for estimation of the proportions of organic matter of each type in the mixture, it is practically impossible. The neural network dedicated to diagnosis of the organic matter type only comprises the outputs associated with the basic types. Mixtures of organic matters will therefore be detected from these outputs.

When it is suspected that there is a presence of a mixture of organic matters, the network generally responds by partly activating outputs, as in the case of deterioration or of a great mineral matrix effect. Diagnosing a mixture of organic matters occurs only when all the other possibilities have been dismissed.

There are three main maturation zones. These three zones are defined by means of the following fuzzy sets: Probably immature, Probably in the oil window and Probably in the gas window, obtained by fuzzification of the outputs of the network dedicated to maturation analysis.

The same reasoning as that used for characterization of the basic types is used. It is all the more probable that a given sample is in a given maturity zone as it is unlikely to be in the other two zones.

There are two intermediate maturation zones that are worth distinguishing. The first zone lies between the immature zone and the oil zone, and the second zone lies between the oil zone and the gas zone. They are the initial maturity zone and the wet gas zone respectively. When a sample is in one of these two intermediate zones, the network dedicated to maturation analysis responds by partial activation of the two outputs involved.

The fuzzy sets Probably immature, Probably in the oil window and Probably in the gas window, obtained by fuzzification of the outputs of the network dedicated to maturity analysis, constitute the basic knowledge from which the fuzzy sets characterizing these intermediate zones are defined.

According to the petroleum potential criterion, three rock categories are identified: low petroleum potential rocks, moderate petroleum potential rocks and high petroleum potential rocks. Each one of these categories is defined by a fuzzy set calculated by fuzzification of parameter $S_2$.

The various petroleum potential levels are defined as follows:

Low PP: low $S_2$ moderate PP: moderate $S_2$ high PP: high $S_2$.

Using the production index for accumulation diagnosis has two major drawbacks. The first drawback is due to the fact that an often considerable part of the free hydrocarbons initially present in the sample have volatilized before passing the sample into the pyrolyzer. The second drawback comes from the mathematical definition of the production index, because even for very low $S_1$ values, it is possible to obtain relatively high $S_1(S_1+S_2)$ ratios without there really being a significant accumulation. For example, for $S_1=0.75$ and $S_2=0.25$, a 0.75 production index is obtained whereas, in reality, the amount of free hydrocarbons (given by the value of $S_1$) is very low. The absolute accumulation index (parameter $S_1$) must therefore be taken into account simultaneously with the PI.

Three accumulation degrees are distinguished: low accumulations, moderate accumulations and high accumulations. These accumulation degrees are coded by fuzzy sets whose definition is based on fuzzification of parameter $S_1$ and of the production index (PI).

If one of the indicators ($S_1$ or PI) is low, the accumulation will be low. On the other hand, if both indicators are high, the accumulation will be high. Finally, if at least one of the indicators is moderate and none is low, the accumulation is considered to be moderate.

A hydrocarbon accumulation in a rock is interpreted differently according to whether the sample is mature or not. In fact, an immature sample whose Rock-Eval parameters show a high accumulation is abnormal since the sample still is immature and therefore not supposed to contain a large amount of free hydrocarbons. On the other hand, if the sample is mature, the accumulation is normal since, in the mature phase, the organic matter is converted into free hydrocarbons. The presence of free hydrocarbons in immature samples can be explained by a contamination of the organic matter.

In order to detect the existence of a contamination, two new fuzzy sets are introduced: Noncontaminated and Highly contaminated. These sets are defined as follows: a low accumulation does not lead to contamination, whatever the maturity. A high accumulation is synonymous with contamination if the sample is immature.

Similar cases can also be sought. The object of similar case seeking is to allow the user to make parallels between new samples and samples from known wellbores (those of the example base). This allows lending more weight to an analysis or, on the contrary, to draw the user's attention to the specificity of a new sample. The latter case can occur when the sample in question has Rock-Eval parameters that exceed, for certain values thereof, the limits recommended by the example base.

Given a new sample to be analyzed, in the example base, reference samples are sought that are the closest to the new sample. The reference samples that the system uses as being the most similar to the sample in question depend on the selection of a function referred to as similarity function. The similarity function that is used involves the main Rock-Eval parameters, i.e. TOC, $T_{max}$, HI, OI and CRI.

The similarity function involves the significant extreme values and not the absolute extreme values, and that the values of the Rock-Eval parameters are not directly used, but rather their images by the various saturation functions.

The ratio obtained for each parameter is deducted from the number 1 since it is a similarity function that is sought, and not a dissimilarity function. The values obtained are thereafter weighted so as to give more importance to the most discriminating parameters, in the present case: $T_{max}$ and HI.

The method according to the invention also allows global study of the evolution of the organic matter. By gathering the Rock-Eval data relative to rock samples taken in a single wellbore, in addition to the data relative to the depths at which these samples were taken, the evolution of the organic matter can be followed throughout the maturation process.

Figure 10:
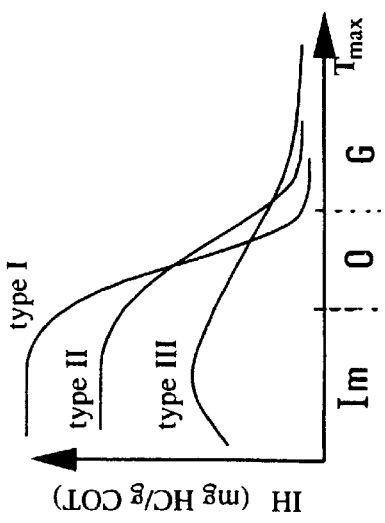
FIG. 10 shows the diagram of evolution of HI.

The evolution of the geologic series as a function of depth is followed. The evolution index used is the hydrogen index. Globally, three evolution stages are distinguished. A first stage (Im) where the values of the HI increase or remain constant, according to the type of organic matter, a second stage where the HI values drop (O), and finally, during the last stage, the HI values stabilize (G). These various stages are diagrammatically shown in FIG. 10.

The rates of change of the organic matter, that can be used in oil exploration, are deduced from the evolution of the HI values as a function of depth.

The object of studying such series consists in tracing the complete evolution of series for which only-data relative to an advanced evolution stage are available. This allows estimation of the rate of change of the organic matter as a function of depth. These rates in turn allows estimation of the hydrocarbons that could migrate during evolution of the source rocks.

The geologic series study is detailed hereafter. What is understood to be a geologic series is a series of samples taken in the same wellbore at variable depths. The objective is to calculate the rates of change for the evolutionary geologic series and to reconstruct the evolution of the geologic series for which only data relative to an advanced evolution stage are available. In both cases, the method consists in finding correlations between various geochemical data. Study of the evolution of a geologic series uses the results of the detailed sample study described above.

The various correlations required for geologic series study are established by means of neural networks. The neural networks are selected for their suitability for handling imprecise data and their capacity to marginalize erroneous data. These assets are of high importance for processing Rock-Eval data. It can be noted that the neural networks are used here as function approximators and not as a classification system, as it is the case for evolutionary series classification.

Given two variables X and Y that are to be correlated by means of a neural network, the initial values of variable Y are referred to as observed values of Y and the values given by the network as a response to the values of X will be referred to as calculated values of Y. Correlating the values of a variable X with those of a variable Y therefore amounts to calculating a function $Y_{cal}=F(X)$.

Figure 11:
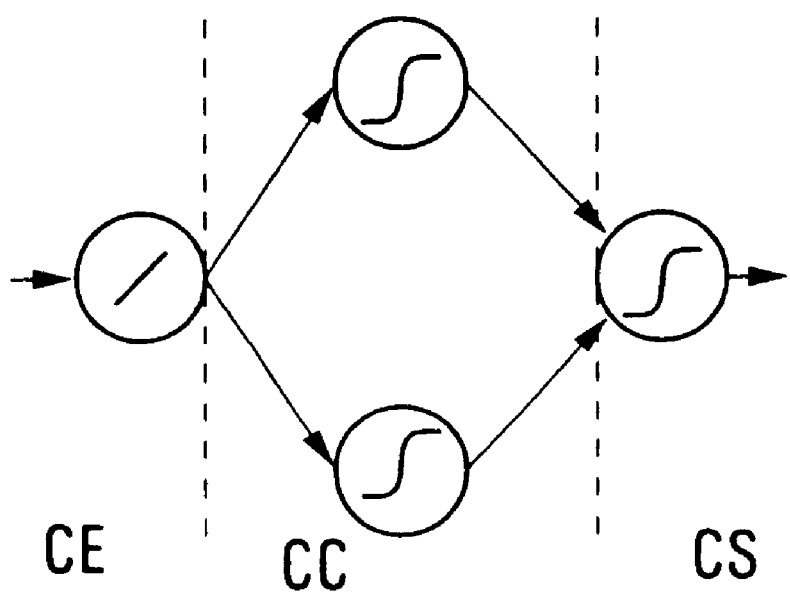
FIG. 11 shows layers of the neural network.

The neural networks used consist of three layers: an input layer CE, a hidden layer CC and an output layer CS (FIG. 11). A hidden layer CC is necessary because, without a hidden layer, monotone functions are obtained now, the relations existing between the data to be analyzed are not necessarily monotone. The input and output layers contain a single neuron each, since correlations between one-dimensional data series such as, for example, between depths and hydrogen indices, are sought. The number of neurons in the hidden layer has been set by means of the described network response optimization strategy. The network model used in .this chapter is diagrammatically shown in FIG. 11. All the neurons of the model use the logistic function as the activation function, except the input neuron which propagates the values received without modifying them.

It should be pointed out that, in order to have correlations that reflect reality, it is important to have a large number of data. In fact, the multitude of data allows to attenuate the effect of the errors contained in the Rock-Eval data.

A complete series is understood to be a series of samples taken from an immature zone as well as from a mature zone. The object of studying such a series is to calculate the rate of change of the organic matter as a function of depth.

Detailed study of the samples that make up the geologic series studied allows determination of the organic matter type that predominates in the series. Furthermore, the evolutionary characteristics of the organic matter differ according to the origin thereof. In order to obtain significant results, study of the evolution of a series should not involve organic matter of various origins. In order to make the series studied homogeneous, atypical samples are eliminated. A sample is considered atypical if it is not of the organic matter type that prevails in the series. Samples coming from geologic levels for which the mineral matrix effects or adulteration effects are strong are also eliminated.

Figure 12:
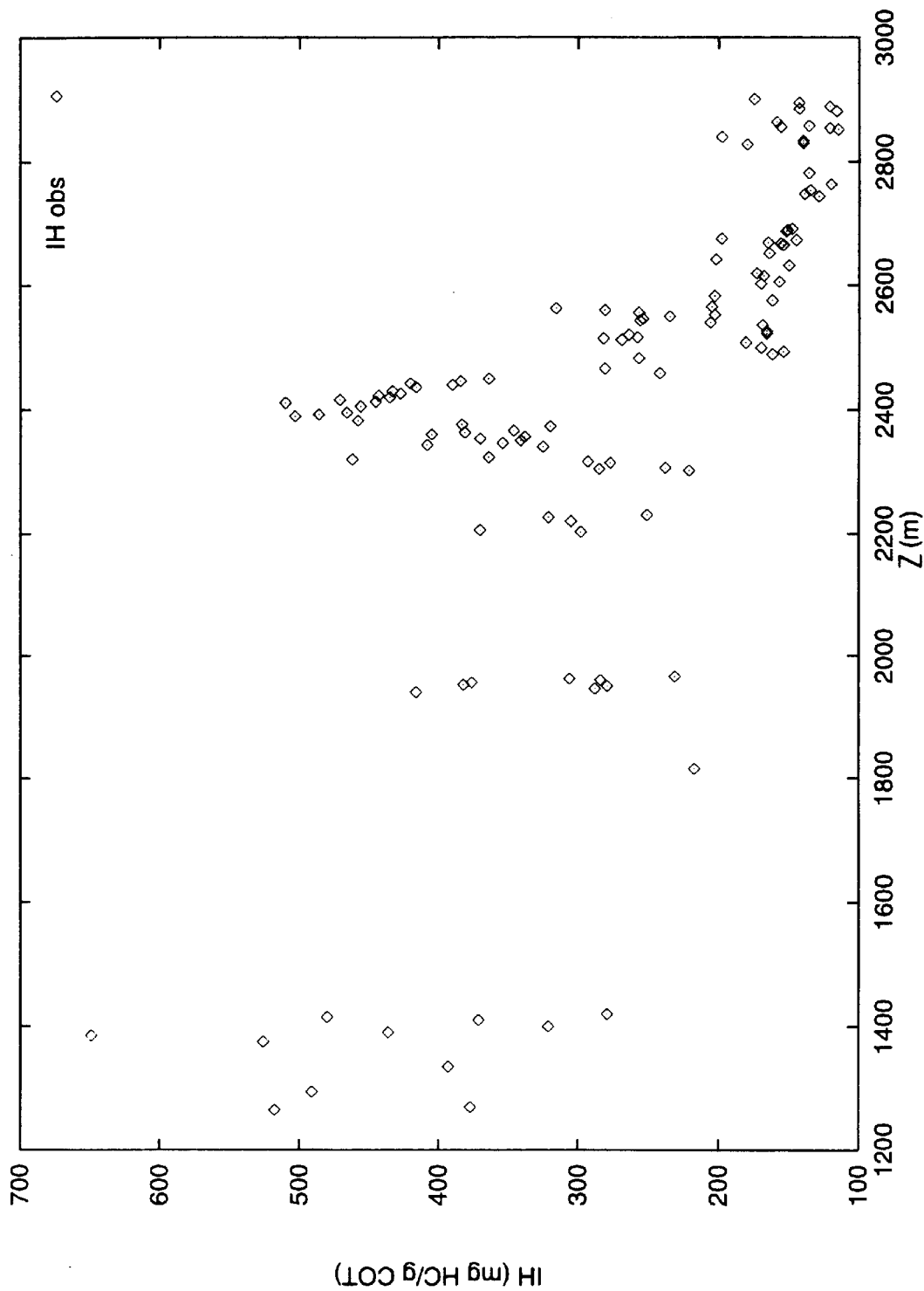
FIG. 12 shows an example of rock measurements: HI versus depth.
Figure 13A:
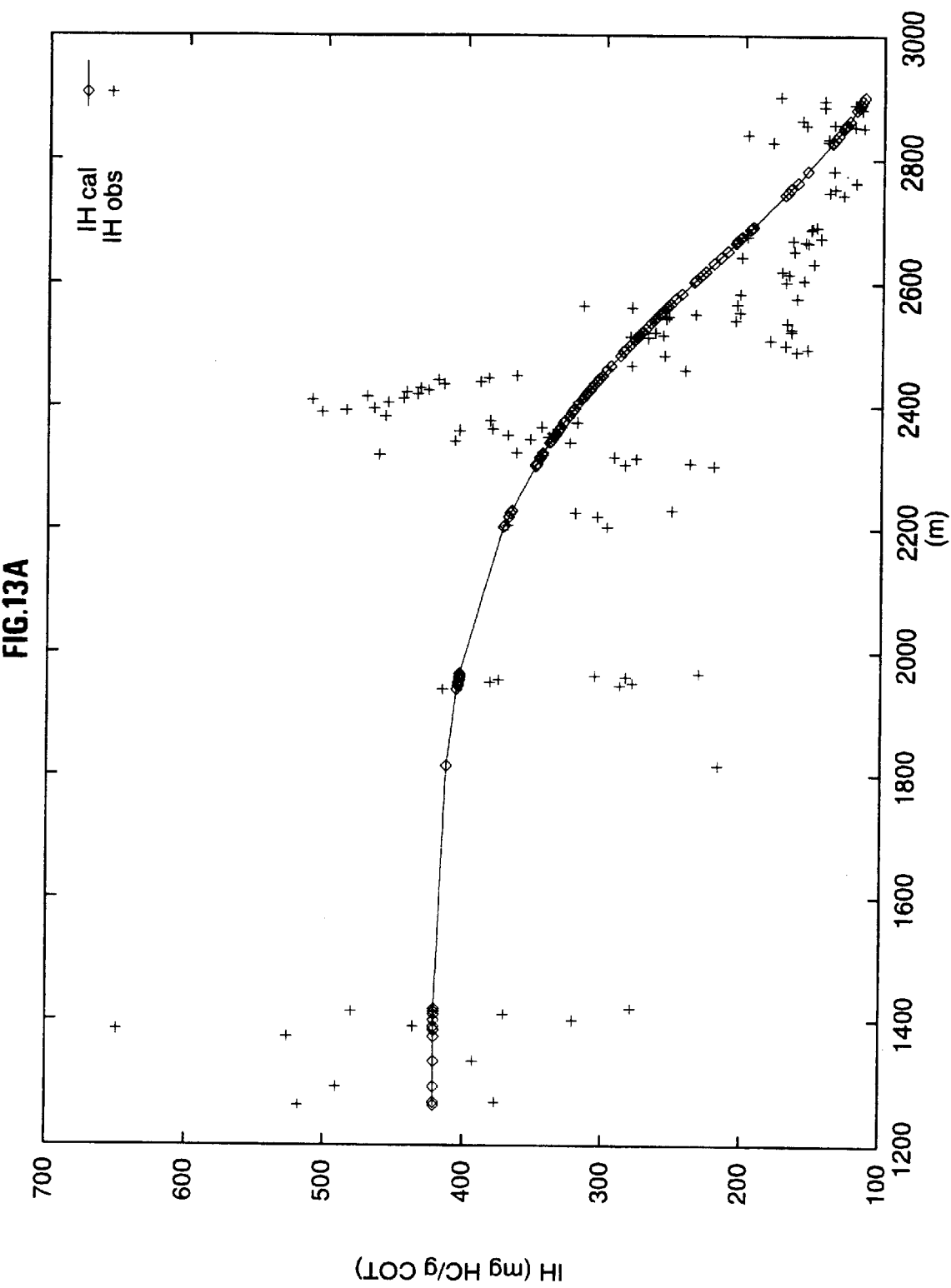
FIG. 13a shows correlation with the method of the invention.

Depth/HI correlation (depth Z): FIG. 12 shows, for a series of samples from the Eastern Paris Basin (France), all the points (IHobs) defined by the HI given by the Rock-Eval pyrolyzer and the depths Z at which the samples were taken. Visibly, the correlation between the depth and the hydrogen index cannot be readily found. A satisfactory correlation is however obtained by means of neural networks (FIG. 13a). The three evolution stages that characterize the type II organic matter can be seen, the series in question being of marine origin: a first phase during which the values of the hydrogen index are practically constant. This phase corresponds to the immature zone. A second phase during which the values of the hydrogen index fall, which is the oil window, and finally a short phase during which the values of the hydrogen index stabilize again, it is the gas window.

This correlation was obtained after 3000 iterations of the training algorithm on 200 points (Depth-HI). The value of the mean square error reached at the training algorithm convergence is 0.01.

The calculated HI values (IHcal) allow estimation of the initial petroleum potential ($IH_0$), then to calculate the rate of change TF corresponding to each depth.

Calculation of the rate of change uses the estimation proposed by R. Pelet in "Evaluation quantitative des produits formés lors de l'évolution geochimique de la matiére organique", Revue de l'Institut Francais du Pétrole, $$TTP = \frac{1200(IH_0 - IH_p)}{IH_0(1200 - IH_p)}$$

Vol.40, 5, 1985: p being the depth at which the sample was taken.

Figure 13B:
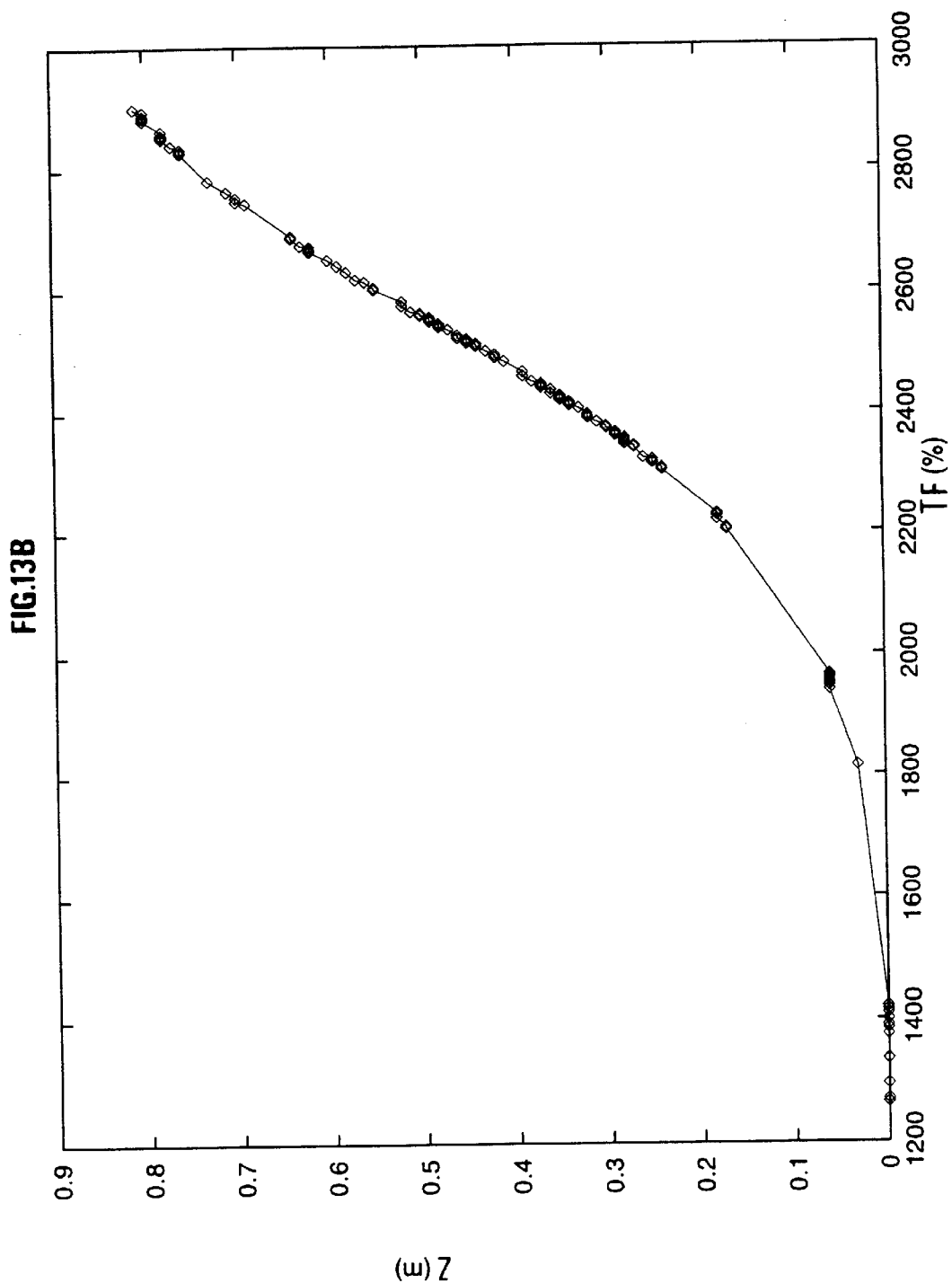
FIG. 13b shows a rate of change TF as a function of depth.

It can be noted that this expression requires the value of the initial petroleum potential ($IH_0$). The $IH_0$ value is given by the mean value of the calculated hydrogen index in the immature zone. Once $IH_0$ fixed, the rate of change TF corresponding to each depth Z can be calculated. The evolution of the rate of change as a function of depth for the series from the Eastern Paris Basin is shown in FIG. 13b.

Study of highly evolved series: the object is to study geologic series at an advanced maturation stage. The problem that arises with such series is that no data relative to the immature zone of the wellbore are available.

Study of highly evolved series is interesting because it allows estimation of the amounts of hydrocarbons that could migrate from the source rock during evolution of the organic matter.

Furthermore, the rock characterization method described above allows determination, with a satisfactory degree of certainty, the origin of the organic matter even if the latter is at an advanced maturation stage. Knowing the origin of the organic matter contained in highly evolved series samples, one sets out to compare the latter with a series of the same origin for which the complete evolution is known.

It has been described how a geologic series can be characterized by the depths and by the corresponding hydrogen indices. Unfortunately, two series that do not come from the same basin do not necessarily have the same geologic data, and consequently it would be risky to compare their evolution on the basis of the depth. On the other hand, for a given organic matter type, the maximum pyrolysis temperature ($T_{max}$) constitutes a standard indicator for evolution since the start of the oil zone and the start of the gas zone are approximately located around the same $T_{max}$ values for the same organic matter type.

The method consists in comparing the highly evolved series with a type series of the same origin, from the relation $T_{max}$/IH. Several intermediate correlations are necessary to make this comparison. The various stages (FIGS. 14a to 14e) of the procedure to be followed are described hereafter.

Figure 15:
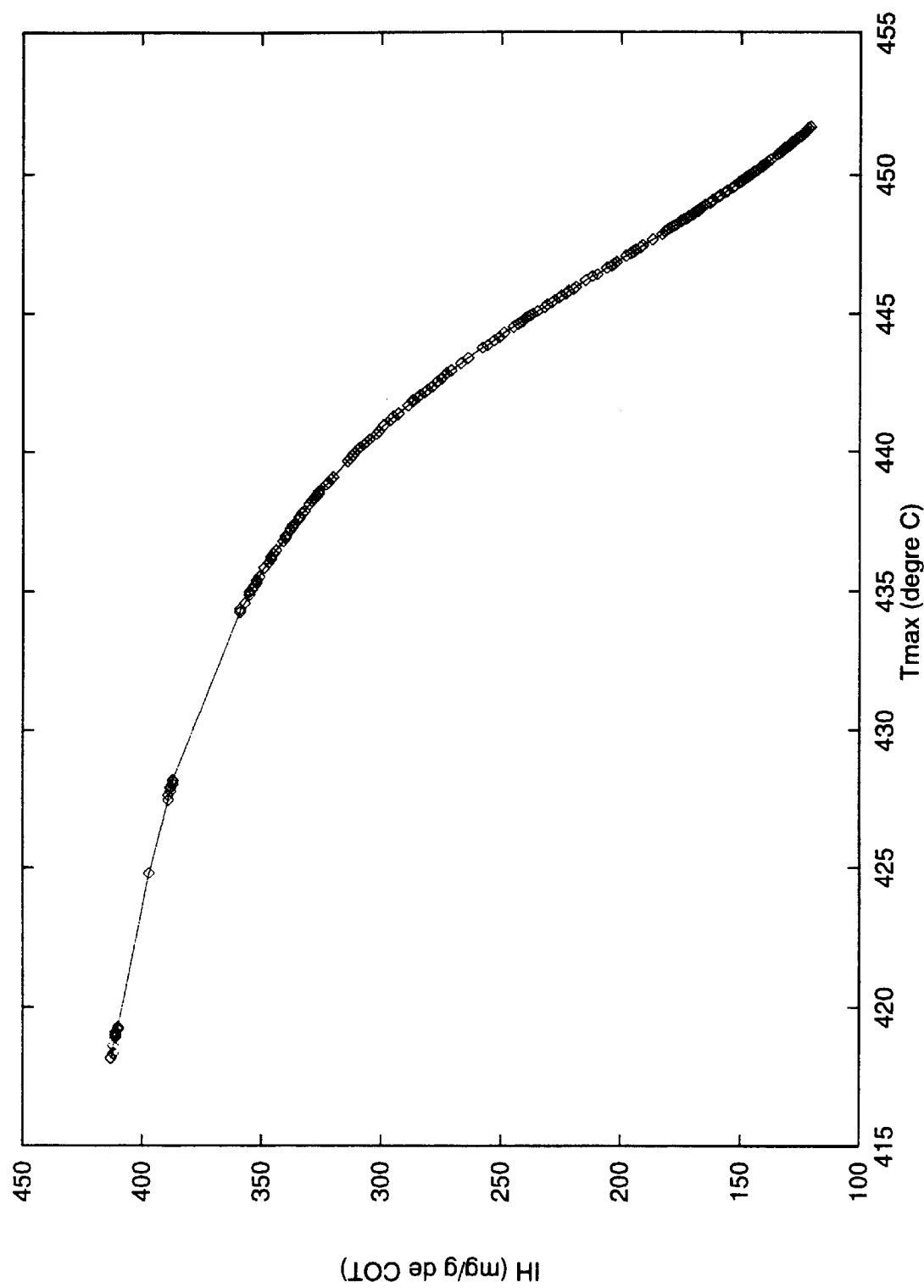
FIGS. 15 and 16 show two examples of series.
Figure 16:
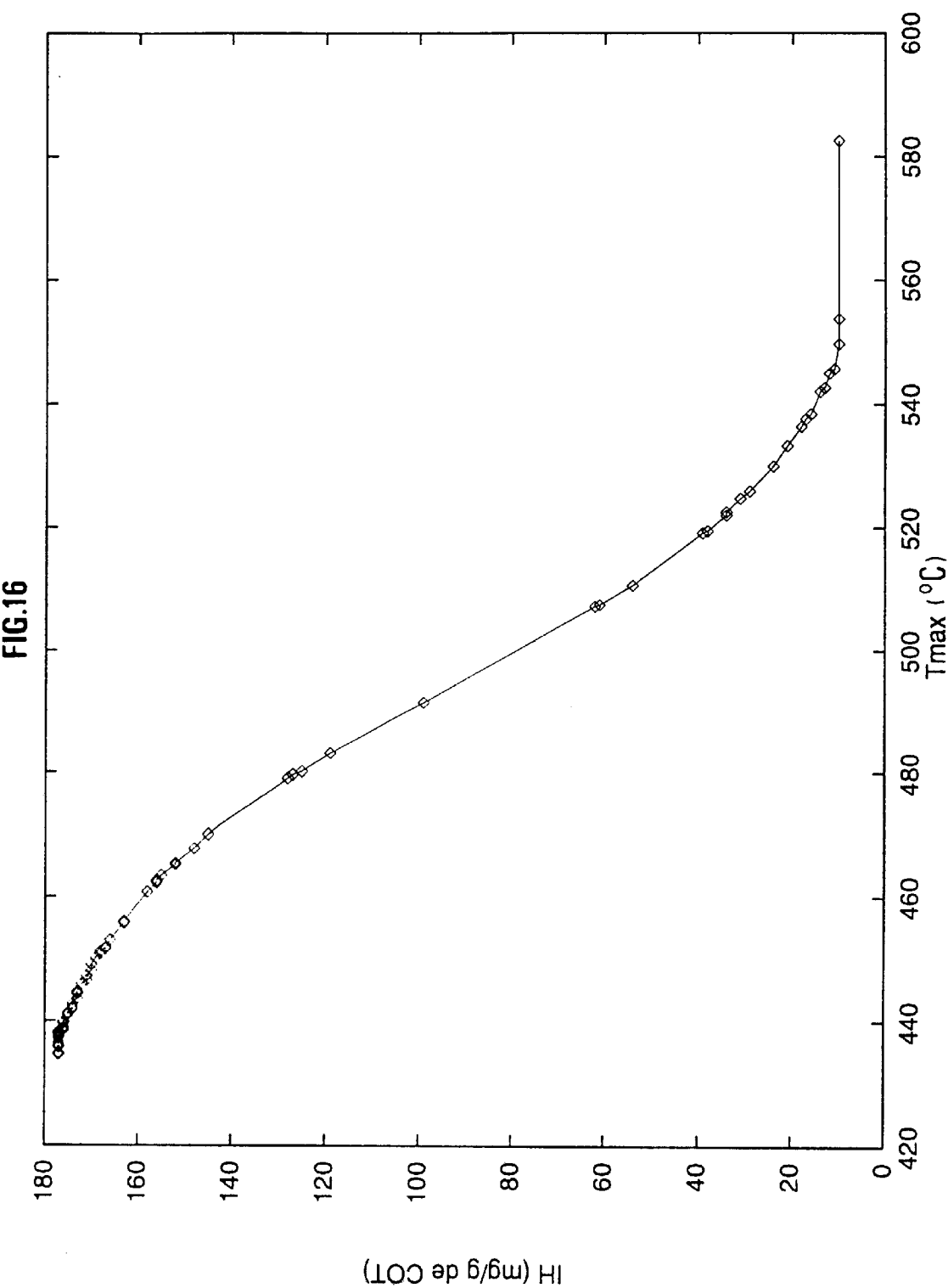

Three evolutionary series are used as type series (one series for each organic matter type). These series come from the Green River Shales series of the Utah Basin (United States) for type I, from the Melarchez wellbore in the Eastern Paris Basin for type II and from the Gironville wellbore, also in the Eastern Paris Basin, for type III. The variation of the HI as a function of $T_{max}$ for the last two type series is shown in FIGS. 15 and 16.

Figure 14A:
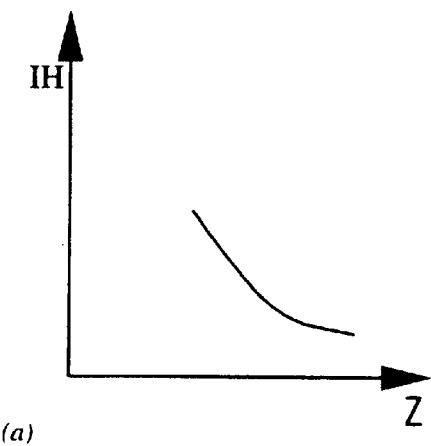
FIGS. 14a to 14e show various stages of the present procedure.

Depth/HI correlation: this correlation has already been described. Its purpose is to correct the observed values of the hydrogen index HI by taking account of the depth Z (FIG. 14a).

Figure 14B:
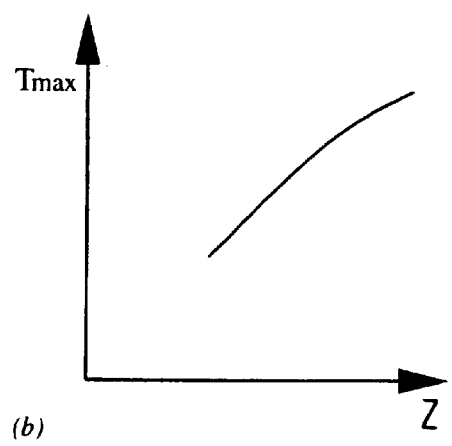
Figure 14C:
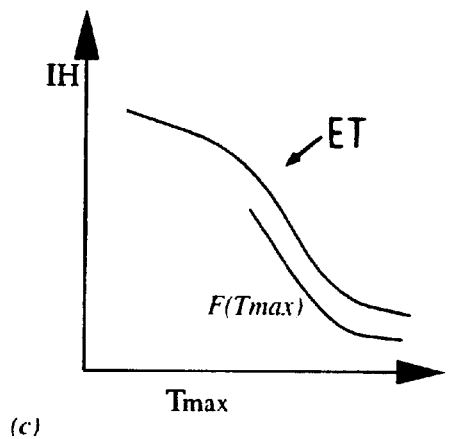

Depth/$T_{max}$ correlation: this correlation allows avoiding irregularities in the values of $T_{max}$, which can be due to the organic matter coming up to the surface or to measuring errors. The neural network used is the model shown in FIG. 11, except that the hidden layer contains only one neuron. A single neuron is sufficient for calculation of the present correlation, because the variation of $T_{max}$ as a function of the depth Z is nearly linear for all organic matter types (FIG. 14b).

$T_{max}$/HI correlation the next stage (FIG. 14c) consists in correlating the calculated values of $T_{max}$ and the calculated HI values obtained from the previous two correlations. It should be pointed out that calculation of the $T_{max}$/HI correlation for a highly evolved series does not involve the $T_{max}$ values corresponding to the immature zone, since the type evolution ET of the series in this zone is not available.

Furthermore, by denoting the function resulting from the. $T_{max}$/HI type correlation by F, F associates the values of the type HI with the values of $T_{max}$ (FIG. 14d).

HI/$HI_{type}$ correlation: the type values of the HI given by function F are matched with the HI values calculated by means of the $T_{max}$/HI correlation of the highly evolved series. This matching is carried out on the basis of equal values of $T_{max}$.

Figure 14D:
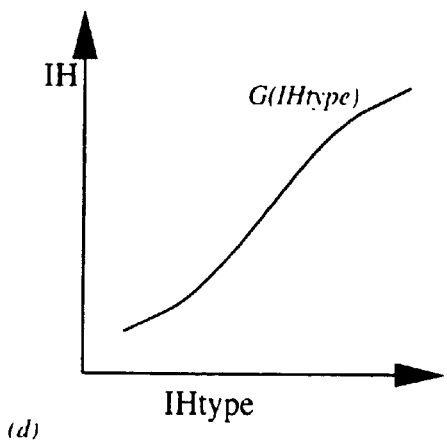

The function that associates the calculated HI values with the HI type values being denoted by G, the function $IH_{cal}$=G ($IH_{type}$) is illustrated in FIG. 14d.

Figure 14E:
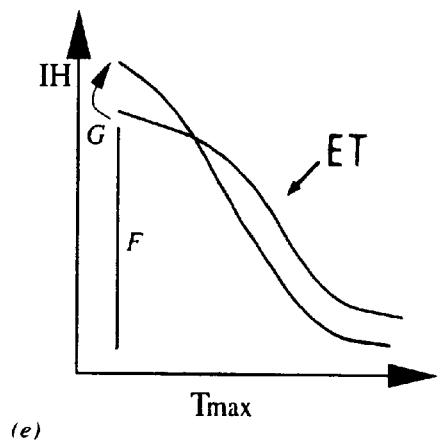

By means of functions F and G, it is possible to calculate an estimation of the values of the HI corresponding to the $T_{max}$ of the immature zone, values that were not available in the initial series. Let $t_{max}$ be a given value of $T_{max}$ belonging to the immature zone. The image of $t_{max}$ is first calculated by means of function F. The HI type value is obtained corresponding to $t_{max}$: $ih_{type}$=F($t_{max}$) (FIG. 14e).

The image of $ih_{type}$ is then calculated by means of function G. The value GoF ($t_{max}$) obtained is the estimation of the hydrogen index corresponding to value $t_{max}$. Thus calculating the HI values for all the values of $T_{max}$ in the immature zone allows to obtain an estimation of the complete evolution of the HI as a function of $T_{max}$ for the highly evolved series.

Figure 17A:
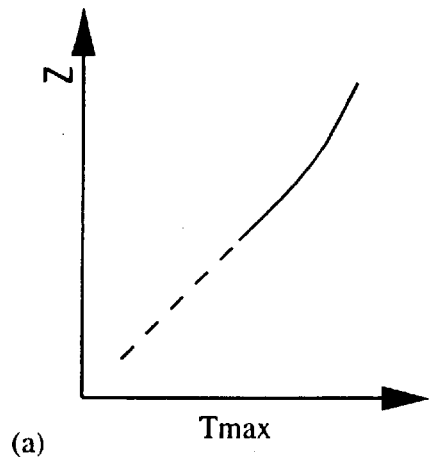
FIGS. 17a to 17d show principle steps for obtaining the initial petroleum potential.

Calculation of the rate of change TF of the organic matter as a function of depth is possible, for a highly evolved series, only if the evolution of the HI as a function of depth is known. Now, for the moment, the evolution of the HI as a function of $T_{max}$ has been reconstructed. To find the evolution needed (HI as a function of depth), a correlation that gives the depth as a function of $T_{max}$ is calculated for the highly evolved series (FIG. 17a). The $T_{max}$/Depth correlation allows to associate depths with the $T_{max}$ values corresponding to the immature zone, although it is calculated only from data coming from the mature zone. Such an extrapolation is acceptable tanks to the quasi-linearity of the variation of $T_{max}$ as a function of depth.

Figure 17B:
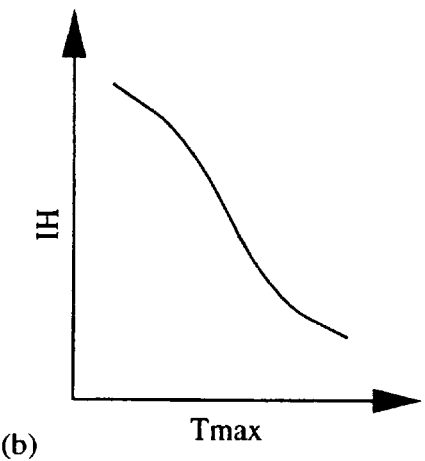
Figure 17C:
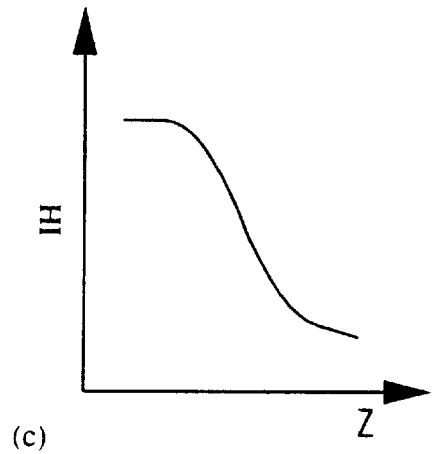

The evolution of the HI as a function of depth is deduced from the complete evolution of the HI as a function of $T_{max}$ and from the $T_{max}$/Depth correlation; it is therefore sufficient to match the depths and the values of the HI that are associated with the same value of $T_{max}$ (FIGS. 17b and 17c).

Figure 17D:
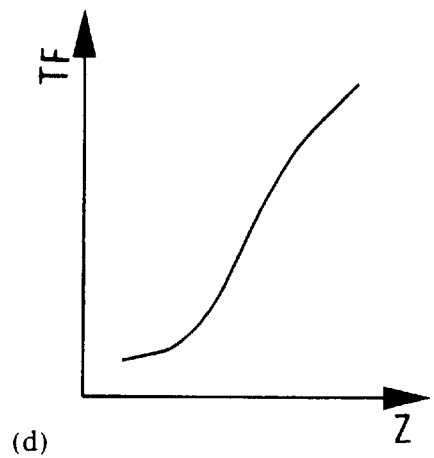

Once the evolution of the HI as a function of depth is calculated, the initial petroleum potential can be estimated by means of the mean value of the calculated hydrogen index and the rate of change TF can be calculated (FIG. 17d).

Application example:

Study of a type III evolutionary series: consider the geologic series consisting of samples from the Gironville wellbore of the Paris Basin Lias (France). This wellbore was drilled in a coal rock containing organic matter at various maturity stages. The distribution of the samples according to the type and to the maturity of the organic matter is given in FIG. 18.

Figure 19B:
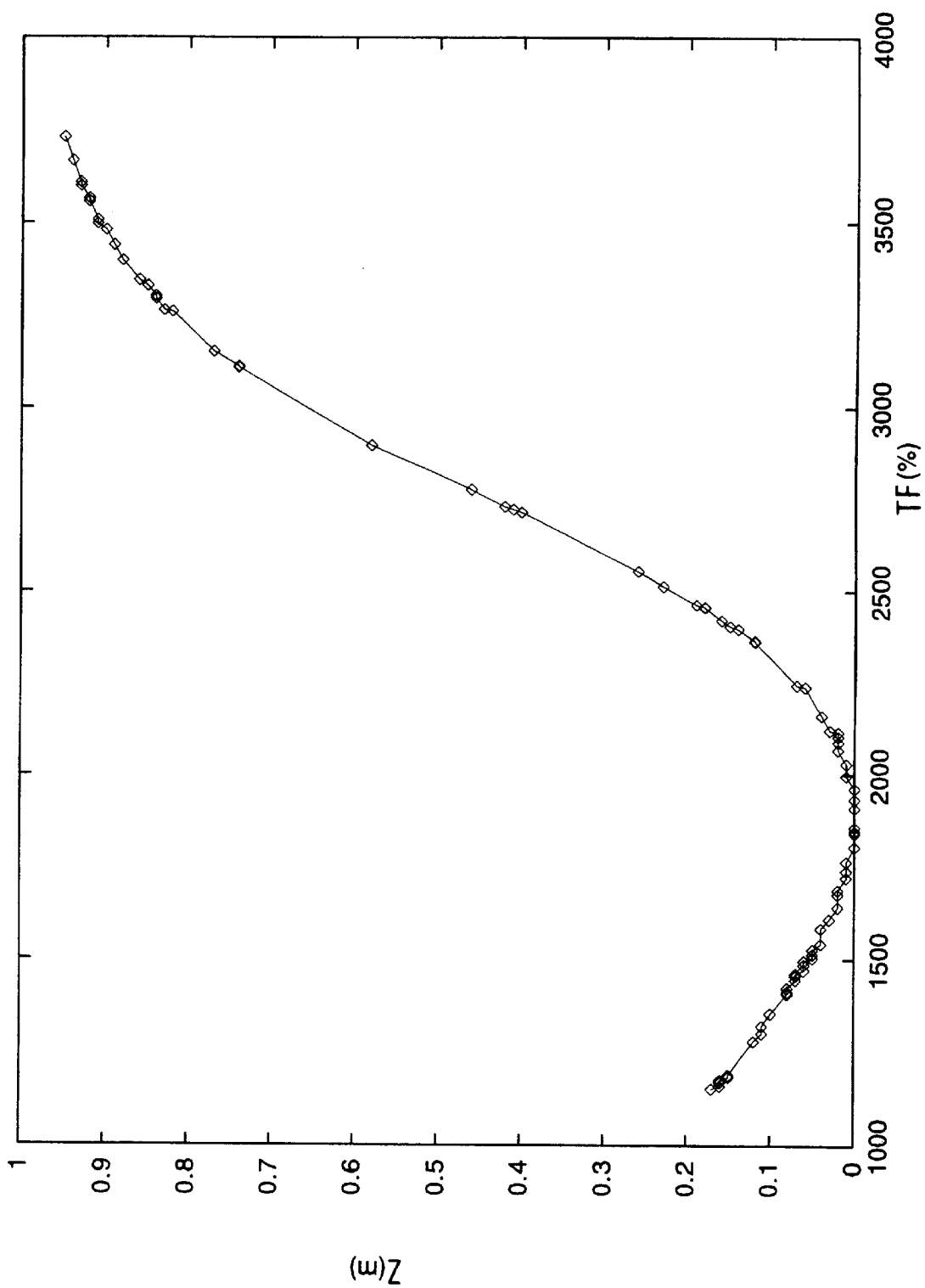

After elimination of the atypical samples, the system establishes the evolution of the HI as a function of depth (see FIG. 19a). The variation of the rate of change TF as a function of the depth Z is thereafter deduced from the previous evolution (FIG. 19b).

Study of a highly evolved series:

The aforementioned series is used again (Balazuc1 wellbore in the South-Eastern Basin in France). It should be reminded that, in this series, the samples were taken in a mature (in the oil window) or very mature zone (in the gas window). The procedure described above is followed to find the evolution of the series in the immature zone and in the initial maturity zone.

Figure 20A:
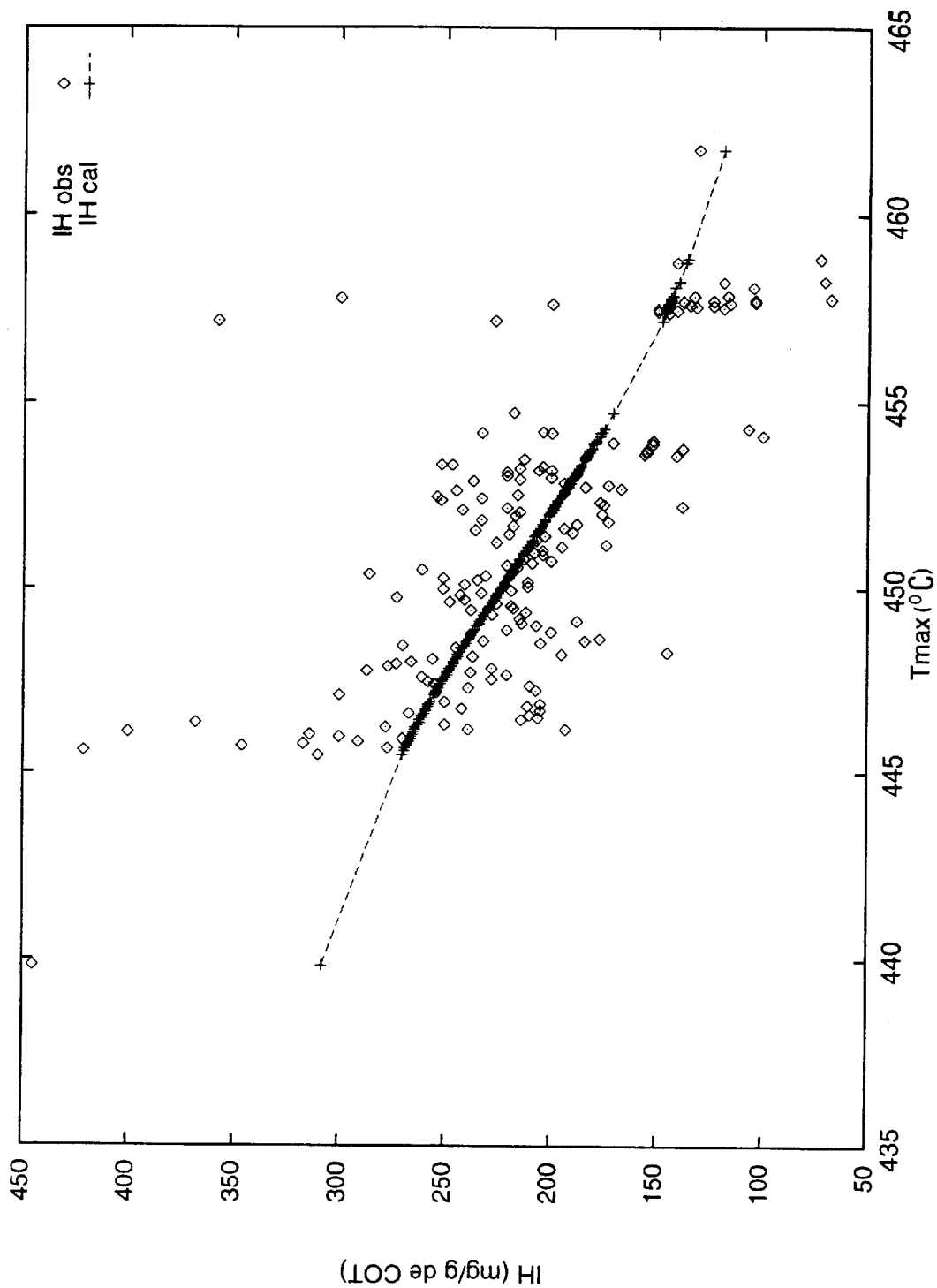
FIGS. 20a and 20b show correlation of Z/Tmax and Z/IH for a highly evolved series.
Figure 20B:
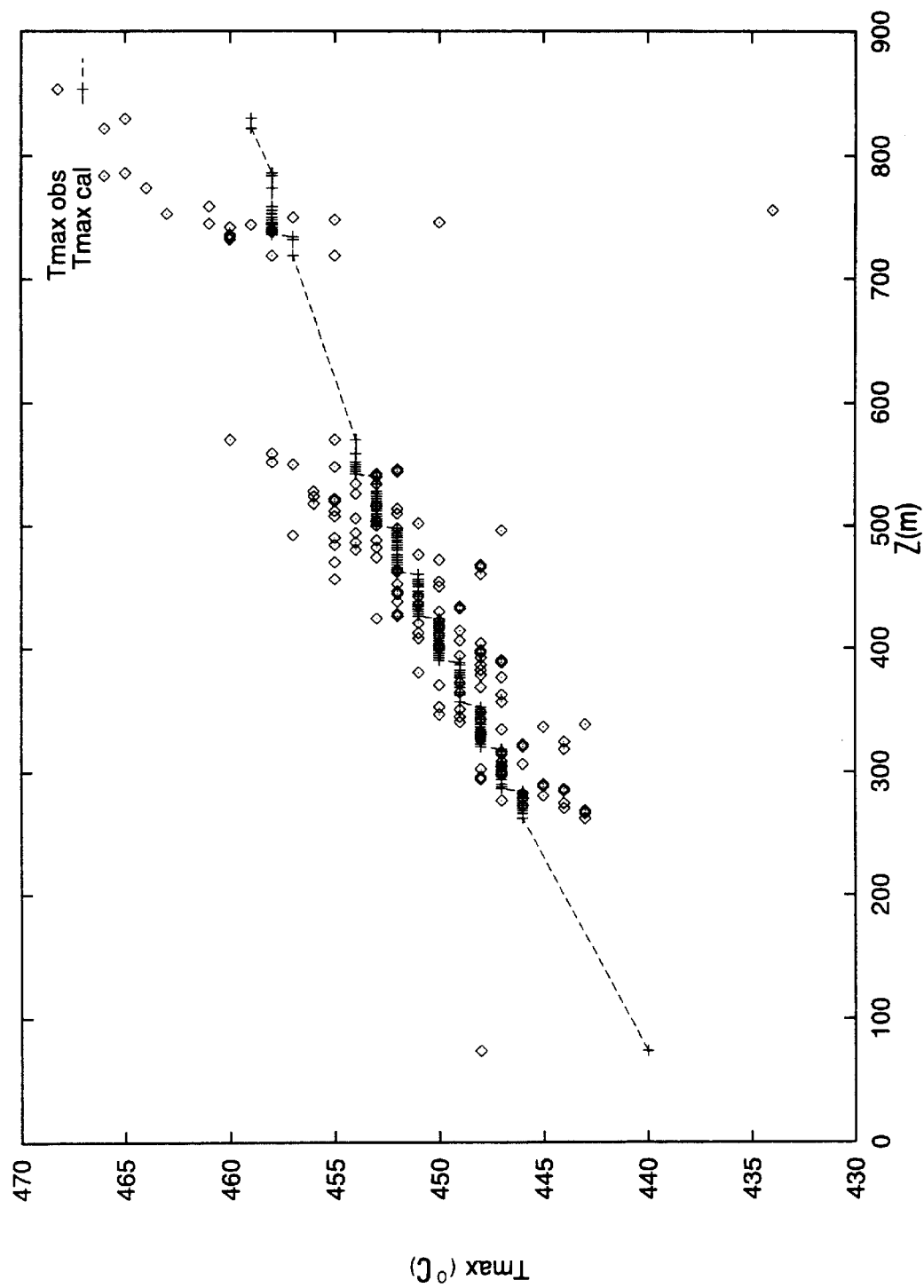
Figure 21A:
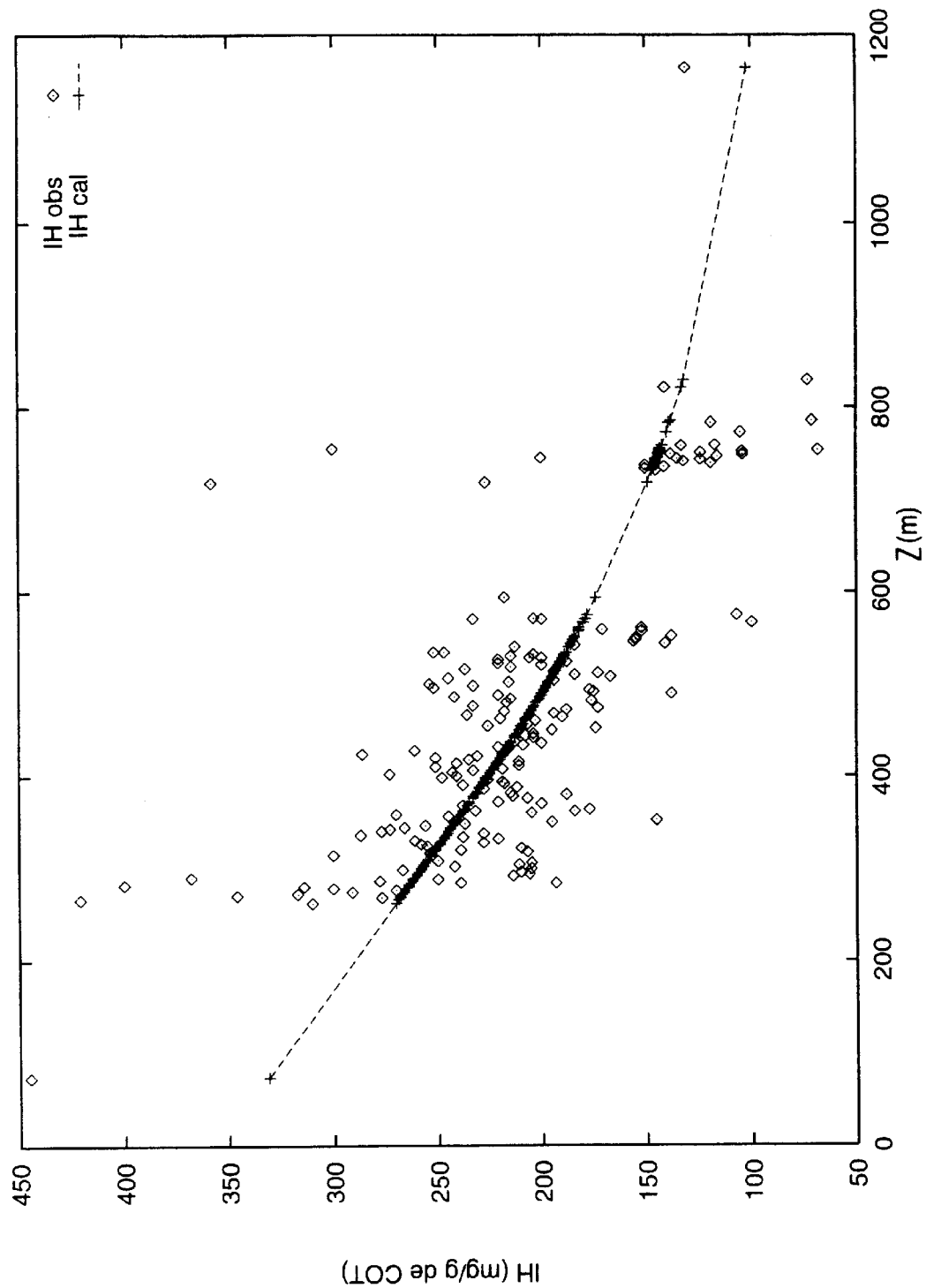
FIG. 21a shows the correlation Tmax/IH.

The Depth/$T_{max}$ and Depth/HI correlations are first established (FIGS. 20a and 20b). Once the values of $T_{max}$ and the values of the HI corrected, they are matched. The $T_{max}$/HI correlation of FIG. 21a is obtained. It can be noted that only the mature zone is involved in this correlation (i.e. the zone for which data are available).

Figure 21B:
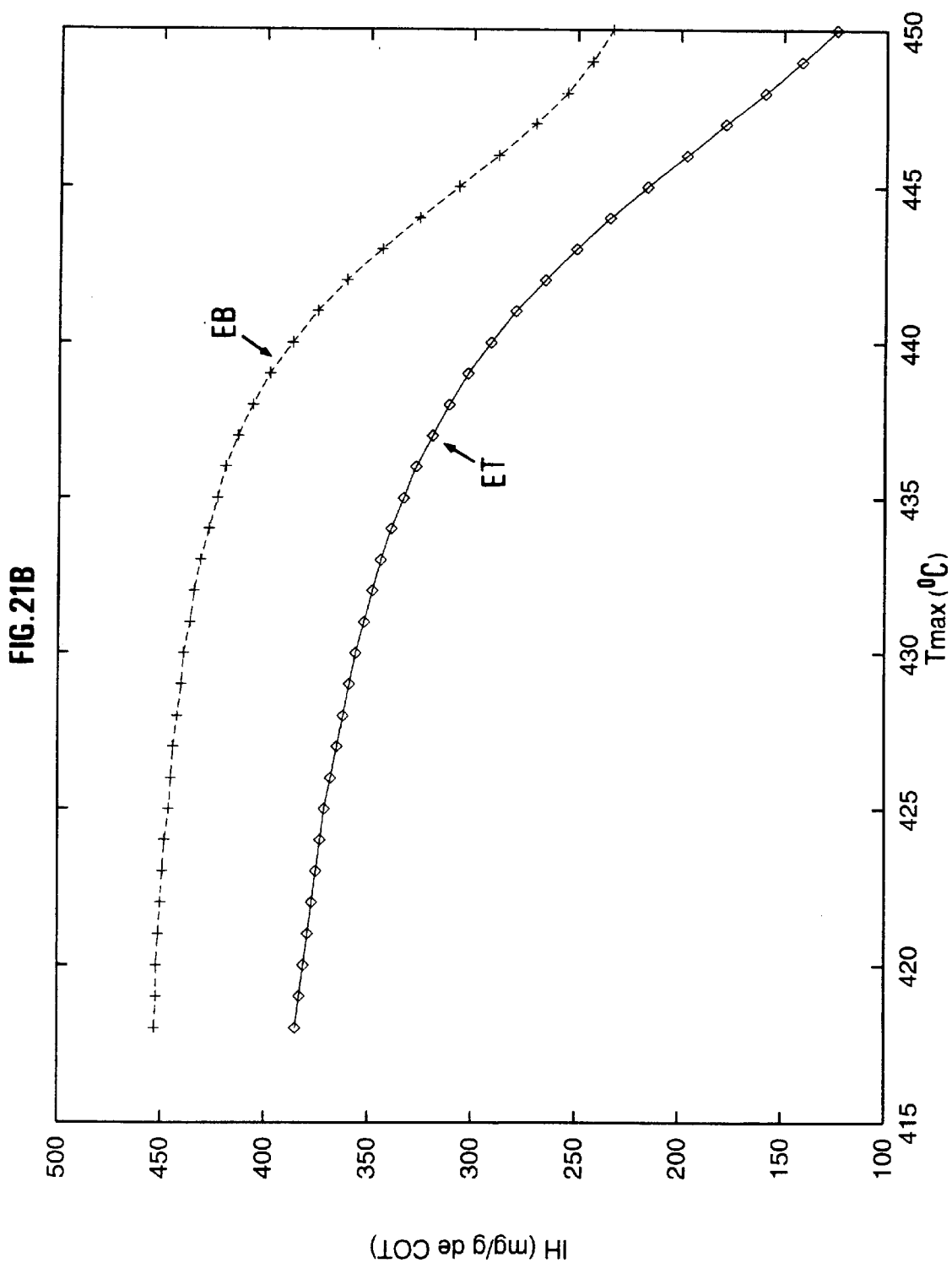
FIG. 21b shows the evolution EB of the evolved series.

The next stage consists in considering a type series ET having the same origin as the Balazuc1 series (marine origin) in order to complete the evolution of the Balazuc1 series in the immature zone as well as in the initial maturity zone. The complete evolution EB of the Balazuc1 series is obtained by following the stage described. See FIG. 21b.

Finally, in order to estimate the rates of change of the organic matter as a function of depth, the variation of the HI as a function of depth is established by means of the aforementioned procedure.

In order to present the advantages afforded by the present invention more clearly, a detailed study of a wellbore drilled in the SM Basin in the United States is described hereafter. The evolution of the organic matter all along this well is studied. Finally, we show with another well how it is possible to find the initial evolution of a highly evolved geologic series.

Before starting interpretation of the pyrolysis data proper, the method provides general information on the samples of the basin, notably the number of samples, possibly the list of the samples that have been eliminated from the study, and the cause of their elimination.

An analysis consists of the essential characteristics of the organic matter that can be deduced from the Rock-Eval parameters and that can be helpful for oil exploration. These characteristics are: the organic matter type, its degree of maturation, the petroleum potential, and the hydrocarbon accumulations. The method also informs the user if the organic matter has undergone deterioration or in case of great mineral matrix effects. Cases of contamination of the source rock by hydrocarbons coming from elsewhere are also reported.

FIGS. 22 to 25 show the data relative to some samples from the well SM analyzed by means of the method. Most of the samples taken in this well contain type II organic matter. The well contains immature as well as mature organic matter. FIG. 26 shows the distribution of the samples according to the type and to the maturation of the organic matter.

The user has an additional tool allowing to gain access to type samples (previously stored in a type sample base), which are the most similar, according to a well-determined similarity function, to each of the samples that have just been analyzed. The user can have access to the Rock-Eval parameters and to the detailed diagnoses of these type samples, in order to compare them with the samples he has just analyzed. The sample of FIG. 27 is considered to be the sample from the type sample base that is the most similar to the sample of FIG. 24.

As observed before, well SM contains samples coming from the two main maturation zones, i.e. the immature zone and the mature zone. An evolutionary study of the geologic series consisting of the samples from well SM can therefore be undertaken. However, the atypical samples, i.e. the samples that are not of the dominant type in the series (type II for well SM), first have to be eliminated. Such a precaution is necessary because the various organic matter types do not have the same evolutionary characteristics. Determination of the atypical samples can be achieved automatically by means of the detailed study of the samples described in the previous paragraph.

Figure 28:
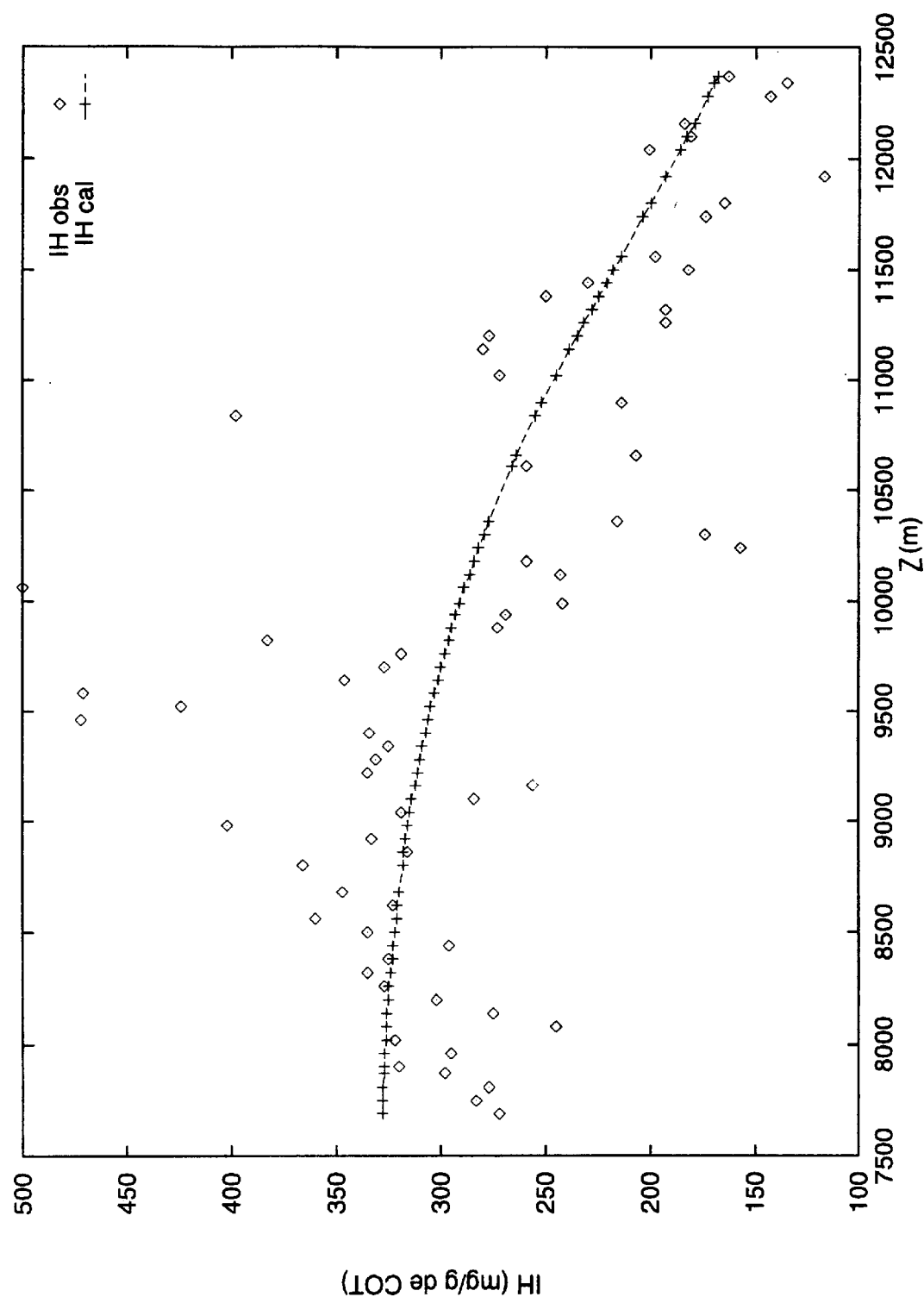
FIGS. 28 and 29 show results obtained by the method of the invention.

Depth/HI correlation: The description of the evolution of a geologic series is given by correlating the values of the hydrogen index observed all along the wellbore with the depths at which the samples were taken. The correlation obtained for the series from well SM is shown in FIG. 28. This correlation has been obtained by means of a multilayer neural network. Calculation of such a correlation is described above.

Figure 29:
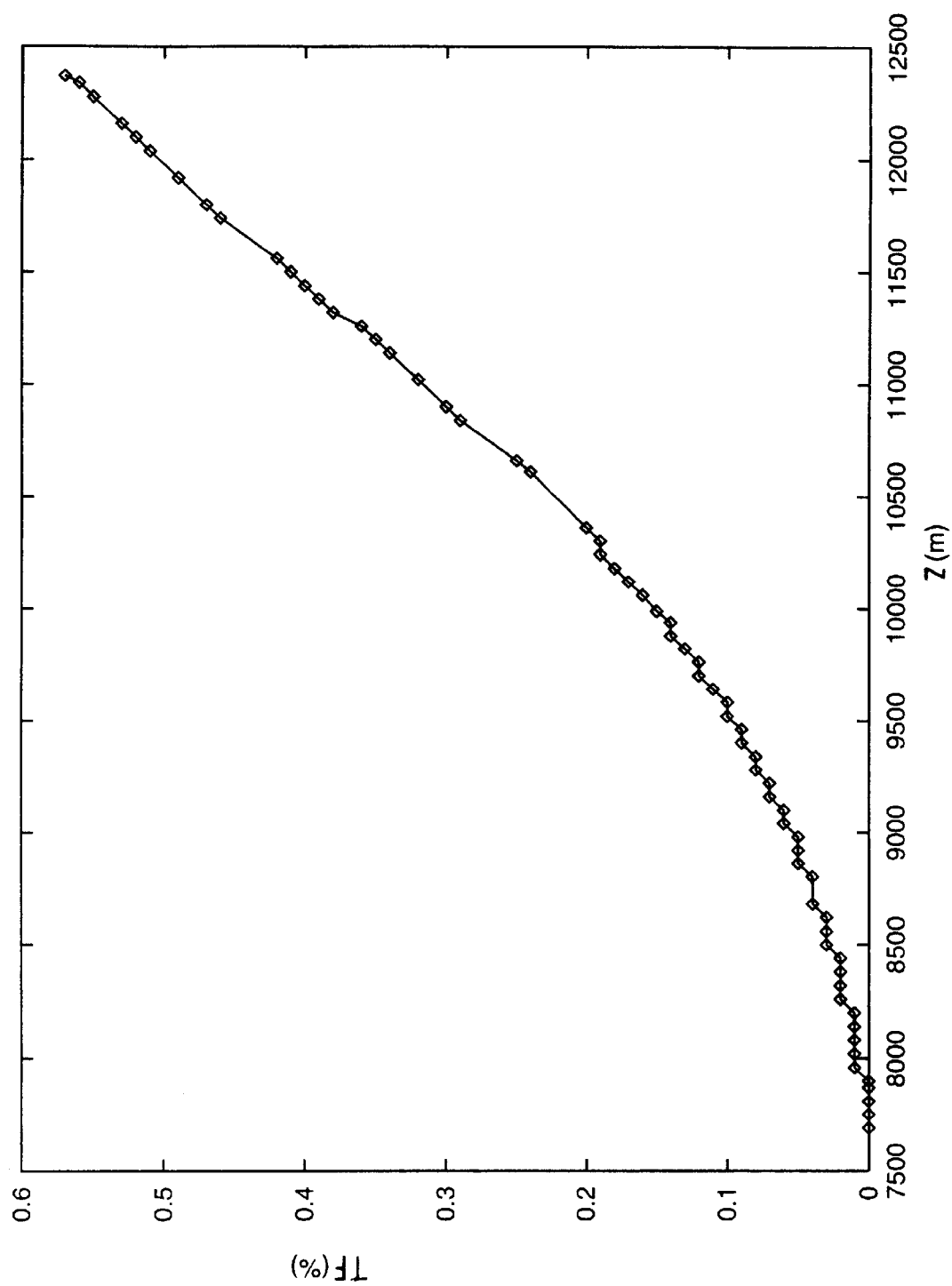

Rate of change: From the calculated values of the HI, given by the Depth/HI correlation, the rate of change of the organic matter, which depends on the HI and on the estimation of the initial petroleum potential, is calculated for each sample. The variation of the rates of change as a function of depth for well SM is shown in FIG. 29.

Study of a highly evolved series: A highly evolved series is understood to be a geologic series for which only data relative to samples containing mature or even very mature organic matter are available. The object of the study of such a series is to find the complete evolution of the series, i.e. also the evolution of the organic matter during the immature stage, which will then allow to give an estimation of the initial petroleum potential.

What is claimed is:

1. A method of providing interpretation of geochemical measurements obtained by pyrolysis of a rock sample in order to obtain information pertaining to organic matter contained in the sample, comprising:

using rock samples with known petroleum characteristics to train an artificial neural network;

using the neural network to obtain parameters which pertain to the organic matter of the rock sample;

using fuzzy sets for interpretation of the parameters at an output of the neural network; and wherein the information pertaining to the organic matter of the sample is determined by a type and a degree of maturation of the organic matter and petroleum potential of the organic matter functionally derived from multivariant correlation functions.

2. A method as claimed in claim 1, wherein an evolved series of rock samples taken during a drilling operation is analyzed by carrying out the steps:

determining, from knowledge of an organic matter type contained in the sample, a correlation function f connecting a hydrogen index (HI) to a maximum pyrolysis temperature ($T_{max}$) for a reference series of the organic matter type;

determining a correlation function g connecting the hydrogen index of the evolved series to the hydrogen index of the reference series;

using the correlation functions g and f to obtain values of the hydrogen index (HI) as a function of depth; and estimating an initial petroleum potential.

3. A method as claimed in claim 2, wherein:

the correlation functions f and g are established with multilayer neural networks.

* * * * *